(12) United States Patent
Naesje

(10) Patent No.: US 7,819,276 B2
(45) Date of Patent: *Oct. 26, 2010

(54) VALVE DEVICE FOR A DRINKING CONTAINER AND A METHOD FOR USING THE VALVE DEVICE

(76) Inventor: Kjetil Naesje, Askeveien 8, Sandnes (NO) N-4314

( * ) Notice: Subject to any disclaimer, the term of this patent is extended or adjusted under 35 U.S.C. 154(b) by 0 days.

This patent is subject to a terminal disclaimer.

(21) Appl. No.: 12/421,424

(22) Filed: Apr. 9, 2009

(65) Prior Publication Data

US 2009/0194548 A1 Aug. 6, 2009

Related U.S. Application Data

(62) Division of application No. 10/479,906, filed as application No. PCT/NO02/00198 on Jun. 5, 2002, now Pat. No. 7,537,133.

(30) Foreign Application Priority Data

Jun. 5, 2001 (NO) .................................. 20012671
Mar. 1, 2002 (NO) .................................. 20021051

(51) Int. Cl.
*A47G 19/22* (2006.01)
*B65D 51/16* (2006.01)

(52) U.S. Cl. .................. 220/714; 220/717; 220/203.23; 137/510

(58) Field of Classification Search ............ 220/203.01, 220/203.11, 203.16, 203.18, 203.23, 203.25, 220/705, 714, 717; 215/387; 137/510
See application file for complete search history.

(56) References Cited

U.S. PATENT DOCUMENTS

| 2,210,206 | A | 8/1940 | Fisher |
| 2,959,314 | A | 11/1960 | Sanchez |
| 3,746,036 | A | 7/1973 | Du Bois et al. |
| 4,135,513 | A | 1/1979 | Arisland |
| 4,623,069 | A | 11/1986 | White |
| 4,928,836 | A | 5/1990 | Wu et al. |
| 5,297,578 | A | 3/1994 | Scott et al. |
| 5,409,035 | A | 4/1995 | Scott et al. |
| 5,465,876 | A | 11/1995 | Crisci |
| 5,607,073 | A | 3/1997 | Forrer |

(Continued)

FOREIGN PATENT DOCUMENTS

GB 1 453 968 A 10/1976

(Continued)

OTHER PUBLICATIONS

International Search Report for related application PCT/NO02/00198, having a mailing date of Oct. 30, 2002.

*Primary Examiner*—Anthony Stashick
*Assistant Examiner*—James N Smalley
(74) *Attorney, Agent, or Firm*—Andrus, Sceales, Starke & Sawall, LLP

(57) ABSTRACT

A method and device for controlling the flow of liquid from drinking containers, wherein a membrane is movably connected to a valve to form a valve, controlled by negative pressure, for liquid from a drinking container, the force resulting from the pressure difference (P1-P2) across the membrane, opening the valve, even by positive pressure (P3) within the drinking container, caused by a carbonated refreshing drink, for example.

18 Claims, 18 Drawing Sheets

U.S. PATENT DOCUMENTS

| | | |
|---|---|---|
| 5,890,620 A | 4/1999 | Belcastro |
| 5,975,369 A | 11/1999 | Yurkewicz et al. |
| 6,145,695 A | 11/2000 | Garrigues |
| 6,264,166 B1 | 7/2001 | Bowland et al. |
| 6,290,090 B1 | 9/2001 | Essebaggers |
| 6,550,493 B2 | 4/2003 | Williamson et al. |
| 6,758,364 B1 | 7/2004 | Rohrig |
| RE38,692 E | 2/2005 | Wong |

FOREIGN PATENT DOCUMENTS

| | | |
|---|---|---|
| NO | 137258 A | 3/1977 |
| WO | 99/38423 A1 | 8/1999 |
| WO | 01/92133 A2 | 12/2001 |

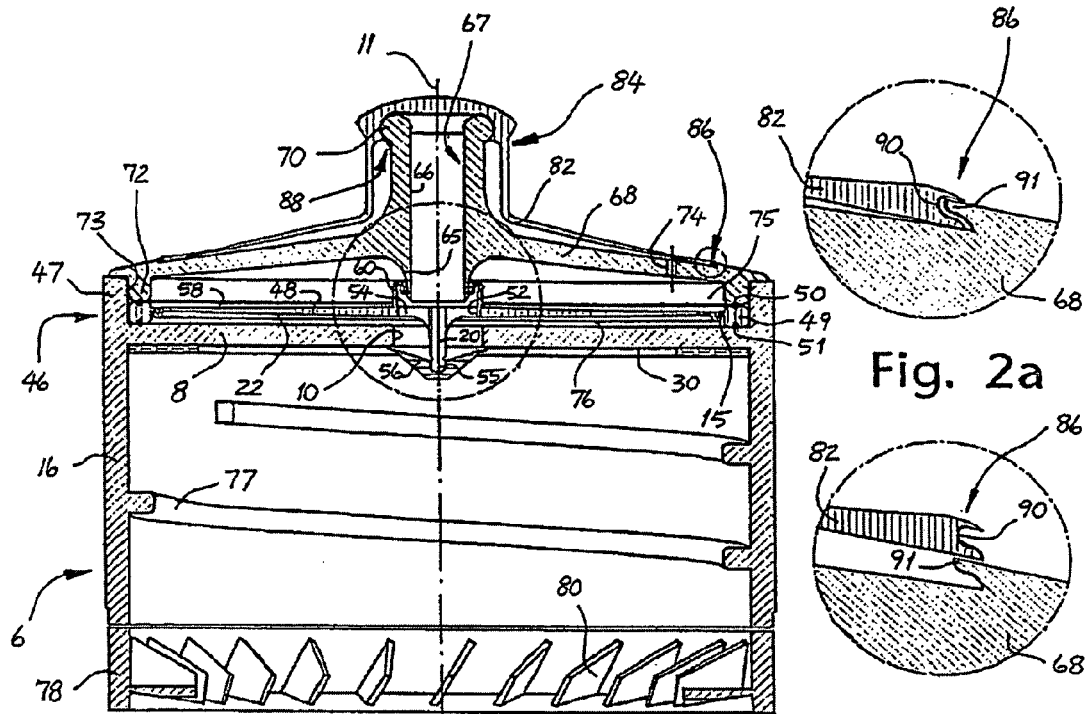
Fig. 2
Fig. 2a
Fig. 2b
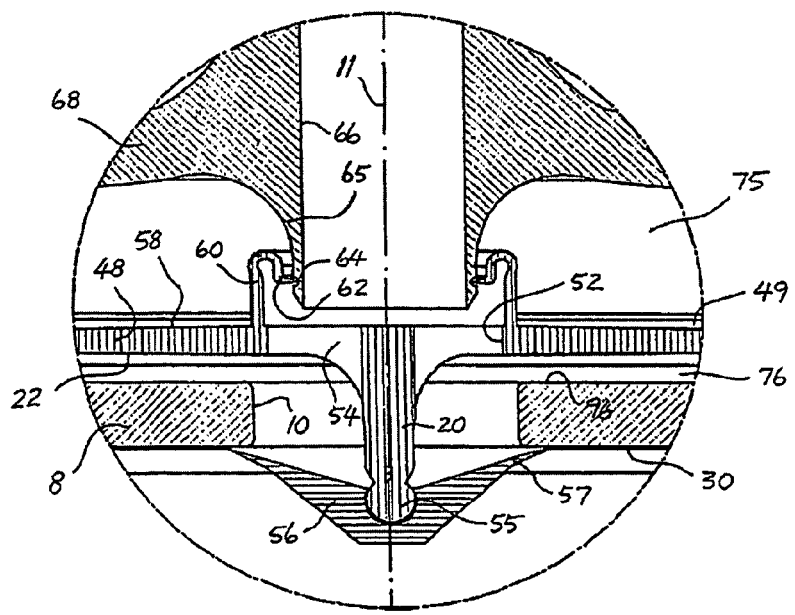
Fig. 3

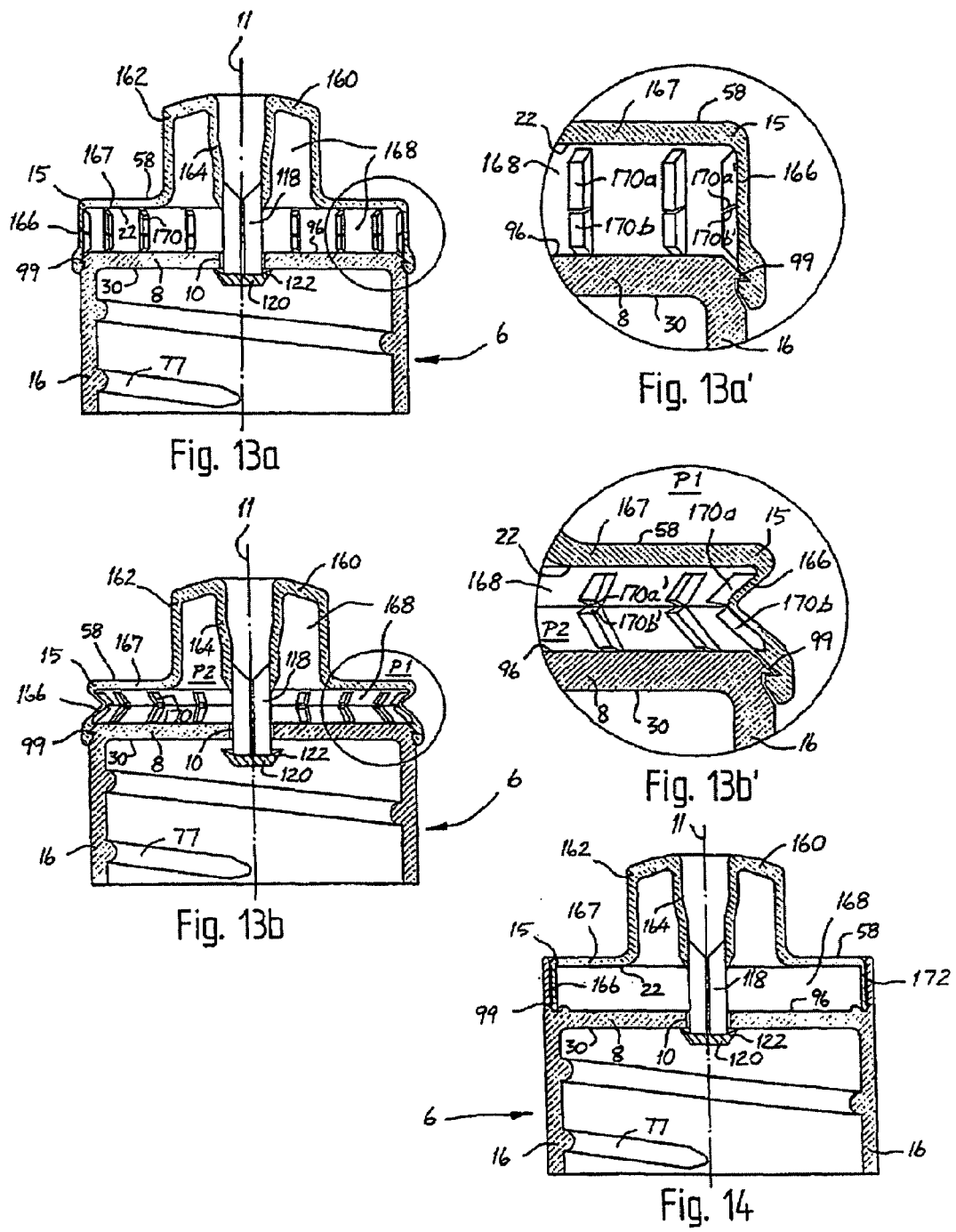

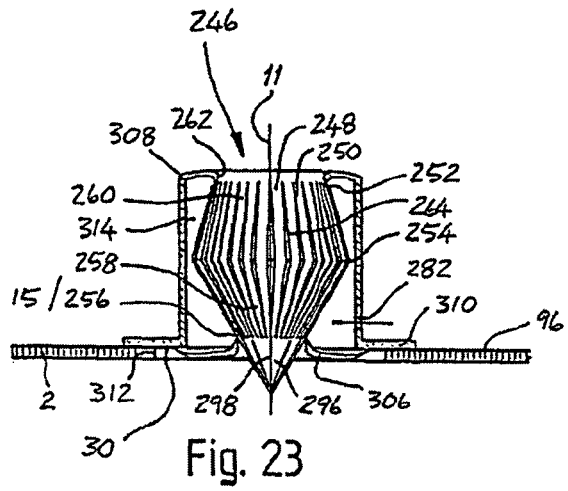
Fig. 23
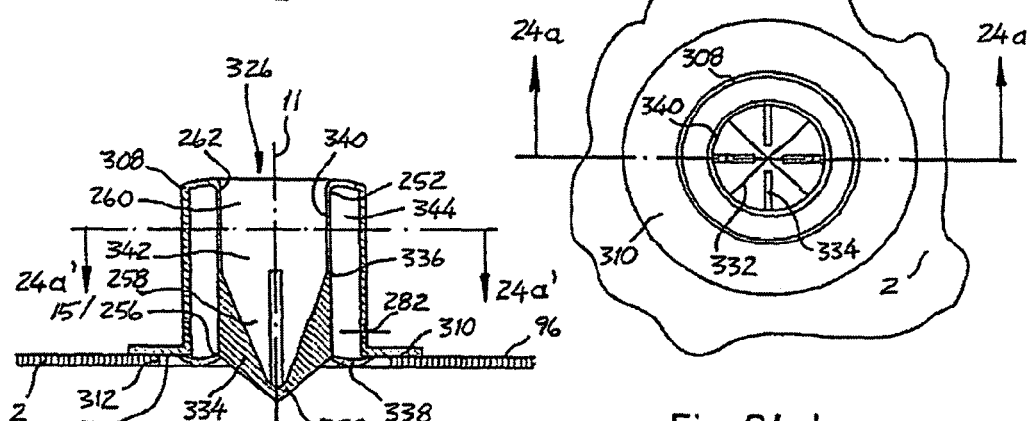
Fig. 24a
Fig. 24a'
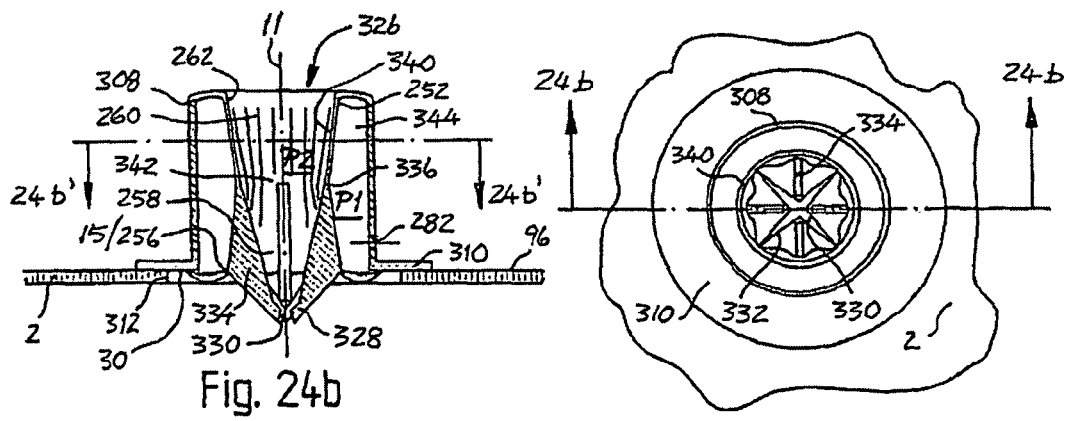
Fig. 24b
Fig. 24b'

VALVE DEVICE FOR A DRINKING CONTAINER AND A METHOD FOR USING THE VALVE DEVICE

CROSS-REFERENCE TO RELATED APPLICATIONS

The present application is a divisional of U.S. patent application Ser. No. 10/479,906, filed Dec. 5, 2003, now U.S. Pat. No. 7,537,133 which application is incorporated herein by reference and which application is the U.S. national phase application of International Application No. PCT/NO02/00198, filed Jun. 5, 2002, which application is incorporated herein by reference and which International application was published on Dec. 12, 2002 as International Publication No. WO 02/098757. The International application claims priority of Norwegian Patent Application No. 20012671, filed Jun. 5, 2001 and Norwegian Patent Application No. 20021051, filed Mar. 1, 2002, which applications are incorporated herein by reference.

FIELD OF THE INVENTION

This invention relates to a valve device for a drinking container, for example a fizzy drink bottle, feeding bottle, carton, bag, jug, tube, paper beaker or plastic cup. The invention also relates to a method for using the valve device and a protective device for a drinking spout of the drinking container.

The fluid inside the drinking container may be easy-flowing one, for example milk, juice, fizzy drink or water, but the fluid may also be a more viscous one, such as yoghurt, soup, pudding or ice. Carbon dioxide or other gases may also pressurize the fluid.

PRIOR ART AND DISADVANTAGES OF THE PRIOR ART

According to the prior art, and in addition to ordinary caps, there are several types of closing devices which prevent a fluid from flowing freely from a drinking container.

U.S. Pat. No. 5,975,369 and U.S. Pat. No. 5,465,876 disclose examples of such closing devices. However, in order to open or close such a device, the user must carry out a mechanical movement of a closing mechanism provided in the device. However, such a device provides poor gas sealing for a pressurized fluid in the drinking container, for example a carbonated liquid, for example a fizzy drink.

NO 137258 discloses a valve device which could prevent pressurized liquid from leaking from a drinking container. However, the device is arranged in such a way that it enhances a valve-closing force from a possible liquid overpressure within the drinking container. The valve device is thus not suitable for containers containing pressurized liquid.

GB 1.453.968 discloses a flow-activated valve device for a feeding bottle, the purpose of the invention being, among other things, to minimize the underpressure that a baby has to use to suck out liquid through an outlet spout of the feeding bottle. The valve device includes a plate between the outlet spout and the feeding bottle. The plate is arranged to a vent for the continuous pressure equalization between the internal cavity of the bottle and the ambient pressure. The plate is also provided with an outlet opening and an external flap resiliently covering the outlet opening of the plate. The flap is propped open by the liquid flowing out of the feeding bottle, after which the flap closes due to its resiliency when the outflow of liquid ceases. Therefore, such a flap valve will open to the outflow of liquid if the pressure in the outlet spout is lower than the pressure inside the feeding bottle, for example if the bottle is held upside down containing sufficient liquid for the flap valve to open. Thereby, the valve is pressure-balanced against the pressure inside the bottle. Due to said vent for continuous pressure equalization, the valve device cannot be used to seal against a pressurized liquid in the bottle.

U.S. Pat. No. 5,607,073 also discloses a valve device for a feeding bottle. Among other things, the valve device consists of an underpressure-activated external seat element resiliently and movably suspended between two supports within an outlet spout is for the bottle. The seat element is provided with a valve seat covering an outlet opening of a plate between the feeding bottle and the outlet spout. When the pressure in the outlet spout is lower than the pressure inside the feeding bottle, the valve seat opens to the outflow of liquid. Thereby, the valve is pressure-balanced against the pressure within the bottle. Like the device according to GB 1.453.968, the valve device according to U.S. Pat. No. 5,607,073 will not seal against pressurized liquids inside the bottle. Moreover, the latter device does not have any vent through which the bottle pressure may be balanced against the ambient pressure. Therefore, as liquid is sucked from the bottle, a gradually increasing underpressure will be created inside the bottle, this forcing the valve seat gradually harder against said outlet opening, rendering drinking from the bottle difficult.

OBJECTIVE OF THE INVENTION

The objective of the invention is to remedy the above-mentioned disadvantages of the prior art.

The present valve device and method are to prevent the spilling of fluid when a user sucks fluid out of a drinking container. By means of said device, the drinking container is sealed automatically when the suction force from the user ceases. By means of the present protective device, a drinking opening of a drinking spout for the container is also protected.

How to Achieve the Objective

The objective is achieved through features as specified in the description below and in the following patent claims.

Among other things, the invention comprises a valve device for a drinking container and a method for the use of the valve device.

In its position of use the valve is connected to at least one opening in a wall portion associated with the drinking container. The wall portion may form part of the drinking container itself, or it may form a wall portion of a cap that is pressure-sealingly associated with the drinking container. The wall portion works as a partition between the interior space of the drinking container and the external surroundings. The valve is arranged to open and close to the outflow of a fluid from the drinking container, the fluid flowing out of a downstream drinking opening. Preferably the drinking opening is arranged to a drinking spout, a drinking straw or other suitable drinking device. Thereby, the present valve device may be releasably-arranged relative to the drinking container.

In principle most valves consist of an activating element and a sealing element, the activating element being associated with and able to move a sealing element between an open position and a closed position. The activating element includes an operating means and at least one bracing element, for example struts or at least one stem, for transmitting activating movements to the sealing element. For example, the stem may be passed through an opening in said wall portion, possibly the stems may be passed through one opening each in the wall portion, such a stem activating a sealing element which is arranged to close its opening in the wall portion. The sealing element, for example a valve head, is attached to the valve stem and is tightened with a specific force against the wall portion, the force being provided, for example, by a resilient unit secured to the valve stem, or the force being provided through the shape of the activating element.

The present invention is based on the activating element being influenced by pressure, and that a pressure force displaces the sealing element into the open position for outflow of the fluid. This is not new relative to the valve devices according to GB 1.453.968 and U.S. Pat. No. 5,607,073.

However, the present activating element is substantially different from the prior art in that the activating element is pressure-balanced against the ambient pressure $P1$ of the drinking container, and that the activating element is arranged to open to fluid outflow whenever the pressure $P2$ of the drinking opening is lower than the ambient pressure $P1$ by a predetermined pressure value. Since the activating element is pressure-balanced against the ambient pressure $P1$ and not against a pressure $P3$ within the drinking container, the activation of the valve in principle will be independent of the pressure $P3$ of the container. Thereby, the pressure $P3$ of the container may exceed the ambient pressure $P1$ without the valve opening to fluid outflow. In contrast, the valve devices according to GB 1.453.968 and U.S. Pat. No. 5,607,073 will open to fluid outflow under corresponding pressure conditions.

Preferably a pressure $P2$ which is lower than the ambient pressure $P1$ by a predetermined pressure value, is provided by a user sucking air and then fluid out through the drinking opening. An underpressure $P2$ is thereby created in the drinking opening. When this underpressure $P2$ is balanced against the ambient pressure $P1$, a resulting differential pressure $(P1-P2)$ is created, moving the activating element by a valve-opening force $F1$ while the differential pressure $(P1-P2)$ is maintained.

According to the invention the activating element of the valve includes a movable membrane formed about an axis on said wall portion, the membrane being provided with at least one flexible zone. The membrane is arranged with a peripheral edge which is pressure-sealingly associated with the outside of the wall portion, and which surrounds the opening (s) of the wall portion. Thereby, a chamber is formed between the membrane and the wall portion. When influenced by pressure, the membrane is moved in such a way that the membrane shape changes. By means of said at least one bracing element the change in the membrane shape is converted into an axial valve-opening force $F1$ that is transmitted to and acts on the sealing element. At least in the position of use, the downstream side of the chamber is pressure-sealingly connected to said drinking opening, so that said underpressure $P2$ may be supplied to the chamber, thereby creating said membrane-moving differential pressure $(P1-P2)$ which opens to fluid outflow. Advantageously, consumption of the drinking container fluid may be carried while continuously admitting air into the drinking container. However, this depends on the type of fluid and the pressure $P3$ prevailing within the drinking container.

The valve device may be associated with a lid that, in its position of use, is connected to the drinking container or a cap thereof. The lid may be shaped as or provided with a drinking spout or teat, through which a user may activate the valve device and drink the fluid in the container. If the lid is pressure-sealingly connected to the drinking container, the lid must be provided with aerating options to the outside of the membrane, for example in the form of at least one vent in the lid. Possibly a controlled delay in the reaction time of the valve device may be achieved by adjusting the size and/or number of the at least one vent. Such an adjustment may also dampen possible membrane oscillations that may occur during use. Said drinking spout or teat may also be placed eccentrically relative to the centre of the lid, for example on a cup or a beaker with a large top surface.

For example, said sealing element may consist of a closable beak or a closable ring, which may be opened or closed to fluid outflow by the activating element. The sealing element may also consist of a valve head with a suitable sealing surface arranged to bear sealingly against a valve seat, for example an annular area around said opening in the wall portion. Alternatively the valve head may be shaped as a plug with a conical sealing surface that may rest in a sealing manner in the opening of the wall portion. The valve head may be made from a soft material or be provided with a separate adapted seal for sealing against the valve seat. Possibly the valve head may be secured to a separate stem via a ball joint. Thereby, the head may move relative to the valve stem and compensate for possible irregularities in said opening in the wall portion. A separate valve stem and/or valve head also renders possible the use of different materials and/or production methods for the two parts.

In order to centre a valve stem in the opening of the wall portion, the opening may be provided, for example, with guides projecting from the opening. For this purpose, a valve stem of a cross-shaped cross section or a perforated and tubular valve stem also may be used. Moreover, both of these stem configurations permit fluid flow through said opening when the stem has been passed through the opening.

In addition to or instead of said at least one bracing stem, the membrane may also be provided with bracing ribs and/or have a bracing configuration, for example by the membrane being provided with suitable corrugations. Thereby, the membrane may convert and transmit a pressure influence into a valve-opening force $F1$ acting on the sealing element of the valve. The membrane may also be assembled from two or more parts having different material properties. For example, the membrane may be arranged with one flexible zone of a flexible material, and one bracing zone of a bracing material. The present valve device may also be assembled from one or more detachable parts, so that cleaning and/or replacement of the part(s) is facilitated.

Forming the membrane with at least one elastic bulge, which communicates with said chamber, may provide a further protection against spillage of remaining fluid in the valve device. In the position of use the bulge(s) thereby is/are exposed to the same underpressure $P2$ as that in said chamber on the inside of the membrane, the bulge(s) thereby shrinking when the valve is open. When the underpressure $P2$ ceases and the pressure is equalized to the ambient pressure $P1$, the bulge(s) will expand elastically, thereby sucking in remaining fluid from said drinking opening, drinking spout, drinking straw or other drinking device associated with the drinking opening.

Further details of the present invention are visualized through the following exemplary embodiments.

BRIEF DESCRIPTION OF THE FIGURES

In the following several non-limiting exemplary embodiments of the present invention are described. Components disclosed in the exemplary embodiments may be used in additional combinations than those disclosed in the examples. For example, all variants of the present valve device may be used on different variants of caps and drinking containers. Correspondingly, all connection variants may be used between relevant parts of the valve device and the different variants of caps and drinking containers. The following figures illustrate the exemplary embodiments, in which:

FIGS. 1a-1b show a cap for a drinking container, the cap being provided with the present valve device, and the figures show the principle mode of operation for the valve device, in which FIG. 1a shows the device in its closed position, while FIG. 1b shows the device in its open position;

FIG. 2 also shows a cap for a drinking container, the cap being provided with one variant of the valve device according to the invention, and the valve device being connected to a lid with a drinking spout and a releasable protective cover;

FIGS. 2a-2b show a section of peripheral details of the lid and the protective cover according to FIG. 2, in which FIG. 2a shows the cover connected to the lid, while FIG. 2b shows the cover disconnected from the lid;

FIG. 3 shows a section of central details of the valve device according to FIG. 2;

FIGS. 5a-27e show further variants of the present valve device.

Moreover, the figures are schematic and may be somewhat distorted regarding their shape and relative dimensions. In the following similar figure details will be indicated essentially by the same reference numerals.

EXEMPLARY EMBODIMENTS OF THE INVENTION

Figure 1A:
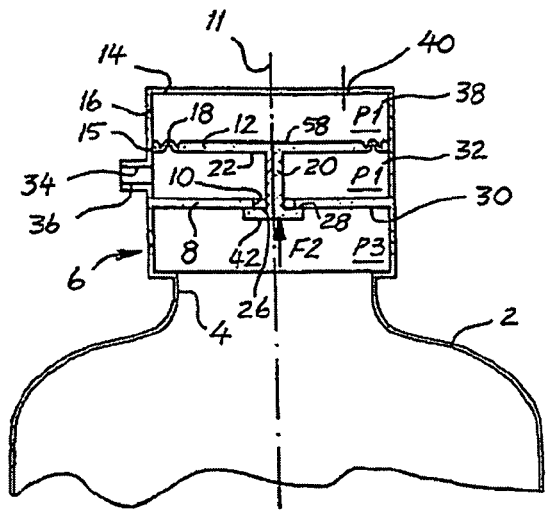
Figure 1B:
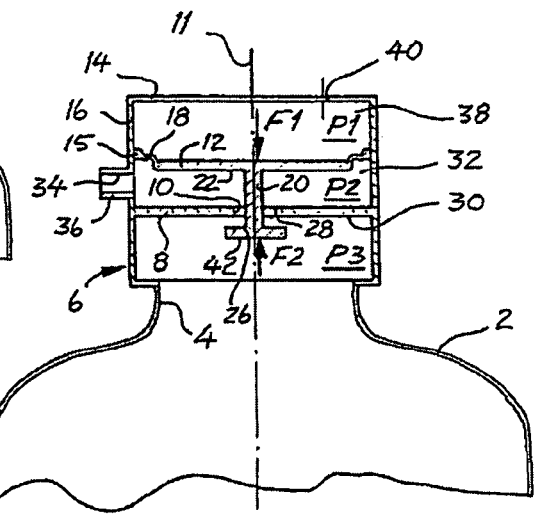
Figure 4A:
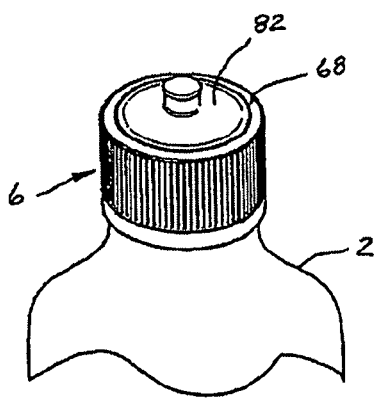
FIGS. 4a-4b show the cap according to FIG. 2 placed on a bottle, each cap being provided with a lid and a releasable protective cover, but the figures showing two different variants of a drinking spout for the cap.
Figure 4B:
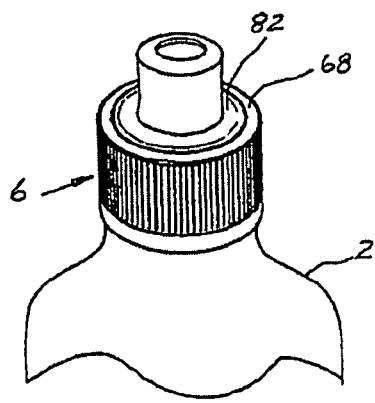

FIGS. 1a-1b show the principle mode of operation for the present valve device. The figures show a drinking container in the form of a bottle 2, which is provided with a cap 6 at its opening 4. The bottle 2 has an internal pressure P3 that may be greater than the ambient pressure P1 of the bottle 2, for example when the bottle 2 contains a carbonated liquid. Internally, the cap 6 is provided with a separating wall portion in the form of a concentric and flat partition 8 provided with a central wall opening 10. The partition 8 is formed about the longitudinal axis 11 of the cap 6. A concentric membrane 12 is disposed between the partition 8 and the end wall 14 of the cap 6. Along its circumferential edge 15 the membrane 12 is pressure-sealingly connected to the side wall 16 of the cap 6, the membrane 12 also being provided with a flexible zone in the form of a peripherally located and concentrically annular corrugation 18. The membrane corrugation 18 is resilient when the membrane 12 moves. A stem 20 is connected to the inside 22 of the membrane 12 and at the centre thereof. The stem 20 projects along the longitudinal axis 11 through said opening 10 of the partition 8, the cross section of the stem 20 being smaller than the diameter of the wall opening 10. At its free end, the stem 20 is provided with a flat valve head 26 arranged to bear pressure-sealingly against a valve seat 28 on the inside 30 of the partition 8. In the cap 6, between the partition 8 and the membrane 12, a suction chamber 32 thus exists which communicates with a drinking opening 34 in the side wall 16 of the cap 6, the drinking opening 34 being defined by a drinking conduit in the form of a tube stub 36. Between the membrane 12 and said end wall 14 an outer chamber 38 exists which is connected with a vent 40 in the cap 6, so that the chamber 38 is pressure-balanced against the ambient pressure P1. The outer chamber 38 thereby works as a protective lid for the membrane 12.

The valve device is activated by suction through the drinking opening 34, whereby an underpressure P2 is created in the suction chamber 32. A resulting differential pressure (P1−P2) thereby will act on the membrane 12 with a pressure force F1 that is transmitted to the valve head 26 via the stem 20. If the pressure force F1 exceeds an oppositely directed pressure force F2 caused by a potential overpressure P3 within the bottle 2, the membrane 12 will be moved towards the wall opening 10, the pressure P3 acting on the top surface 42 of the valve head 26. Thereby, the stem 20 and the valve head 26 will be moved into the open position, cf. FIG. 1b. When the underpressure P2 and the force F1 cease, the membrane 12 will return, due to its flexible zone, to its inactive position and close to outflow, cf. FIG. 1a.

At an overpressure P3 in the bottle 2, the surface area of the underpressure-affected inside 22 of the membrane 12 must be substantially larger than that of the overpressure-affected surface 42 of the valve head 26. Through suitable proportioning of the areas of these surfaces 22, 42, a user may open the valve by sucking a moderate underpressure P2 in the suction chamber 32, even at a relatively high overpressure P3 inside the bottle 2.

FIG. 2 and FIG. 3 show a preferred embodiment of the valve device according to the invention, the device being releasably disposed in an external housing 46 of a cap 6.

FIG. 3 shows enlarged section details of the device. These figures also show a cap 6 provided with a wall portion in the form of a concentric and flat partition 8 with a central wall opening 10. The cap 6 is thereby arranged with an external portion and an internal portion. The external housing 46 is formed concentrically about the longitudinal axis 11 of the cap 6, and the axis 11 is centred in said wall opening 10. The housing 46 exists between said partition 8 and an outer extension 47 of the side wall 16 of the cap 6. A planar membrane 48 is disposed concentrically within the housing 46 and perpendicularly to the axis 11. The membrane 48 is secured to a peripheral mounting ring 49 that is secured pressure-sealingly and releasably to the housing 46. For this pressure sealing, either side of the mounting ring 49 is provided with a gasket 50, 51. This membrane 48 is also provided with a peripheral corrugation 18.

The membrane 48 is also provided with a central drinking opening in the form of an outflow hole 52. A stem 20 is disposed in this outflow hole 52, projecting axially therefrom through the wall opening 10 of the partition 8. The stem 20 is secured to the membrane wall around the hole 52 by means of radial bars 54, fluid flow through the hole 52 thereby being allowed when the valve is open. At its free end the stem 20 is pivotably connected to a conically shaped valve head 56 via a ball joint 55. At its circumference the valve head 56 is arranged as a flexible tapered gasket 57 which may pressure-sealingly engage the inside 30 of the partition 8 and around the wall opening 10 thereof.

On its outside 58 and around the outflow opening 52 the membrane 48 is provided with a flexible annular seal 60. The seal 60 is also provided with an inner connecting collar 62. The collar 62 is arranged to match pressure-sealingly and releasably an annular groove 64 around a first end portion 65 of a concentric drinking conduit 66 in a separate lid 68. In a second end portion 67 of the drinking conduit 66 the lid 68 is shaped as a drinking spout 70. Moreover, an external portion of a lid casing 72 and an internal portion of a cap extension 47 are provided with complementary connecting grooves 73. Thereby, the lid 68 may be releasably attached to the cap housing 46 and outside of the membrane 48. In this connection the lid casing 72 is forced against the membrane's 48 mounting ring 49 and the gaskets 50, 51 thereof, thereby ensuring that the membrane 48 is arranged pressure-sealingly to the partition 8. At the same time said drinking conduit 66 is pressure-sealingly and releasably connected to the outflow hole 52 of the membrane 48. The lid 68 is provided with a vent 74 into an outer chamber 75 located between the membrane 4B and the lid 68, whereby the chamber 75 is pressure-balanced against the ambient pressure P1. The membrane 48 is also placed at a certain distance from the partition 8, so that a suction chamber 76 exists between the membrane 48 and the partition 8. When an underpressure P2 is supplied to the suction chamber 76 via the drinking spout 70, the membrane 48 moves towards the partition 8, whereby the stem 20 and the valve head 56 are displaced and open the valve to fluid outflow.

Moreover, the cap 6 of FIG. 2 is provided with internal threads 77 and an anti-screw stop ring 78 with stop flaps 80. This is prior art. The flaps 80 are arranged to engage barbs, not shown, on a drinking container, thereby preventing the cap 6 from inadvertently being unscrewed from the bottle. The stop ring 78 works as a seal between a drinking container 2 and the cap 6. To break the seal, the circumference of the cap 6 must be subjected to a considerable torsional force. A broken seal thus indicates previous opening of the drinking container 2.

Such an indication of opening is insufficient, however, if the drinking container 2 is provided with a cap 6 with a drinking spout 70, through which a fluid in the container 2 may flow. The lid 68 of the cap 6 and its drinking spout 70 therefore may be provided with a protective device in the form of a protective cover 82 which may cover the lid 68. The protective device is shown in FIG. 2, whereas FIG. 2a and FIG. 2b show details of the cover 82 and the lid 68. The lid 6B and the cover 82 are releasably connected at a primary connecting portion 84 at the drinking spout 70 and at a secondary connecting portion 86 located peripherally at the circumference of the cover 82. At the primary connecting portion 84 the lid 68 and the cover 82 are connected by means of complementary connecting parts of a flange connection 88.

At the secondary connecting portion 86 the lid 68 and the cover 82 are connected by means of a complementary groove 90 and tongue 91 that substantially are directed in a radial direction. Prior to pulling apart the groove 90 and tongue 91 when removing the cover 82 the first time, the lid 68 and the cover 82 are connected at the secondary connecting portion 86, cf. FIG. 2a. Thereafter the interconnection is provided by the primary connecting portion 84, cf. FIG. 2b, this indicating previous opening of the drinking container 2.

In the FIGS. 5a-12b a differently shaped membrane 92, other stem embodiments and other sealing element embodiments are shown, among other things. In all of these figures the valve device is surrounded by a separate lid 94, which is shaped different from the lid 68 shown in FIGS. 2 and 3. By means of a snap connection 99 the lid 94 is pressure-sealingly connected to said separating wall portion 8. The lid 94 is provided with a vent 74 into an outer chamber 98, the chamber 98 and the membrane 92 thereby communicating in a pressure-equalizing manner with the ambient pressure P1.

The FIGS. 5a-9b show the lid 94 pressure-sealingly connected to a partition 8 in a cap 6. In the FIGS. 10-12b the lid 94 is pressure-sealingly connected to a separating wall portion 8 between the valve device and a drinking container 2. Henceforth the separating wall portion 8 will be denoted by the simplified term partition. Moreover, in FIGS. 5a-12b the lid 94 is shaped as a drinking spout 100 surrounding a central drinking conduit 102.

In the FIGS. 5a-12b the membrane 92 is planar on its inside 22 and is disposed perpendicularly to said longitudinal axis 11, the membrane 92 being relatively rigid along its planar portion. In this membrane 92 as well, the outside 58 of the outflow hole 52 is surrounded by a flexible annular seal 104 with an inner connecting collar 106, both components 104, 106 being shaped somewhat differently from the corresponding components of FIGS. 2 and 3. The connecting collar 106 pressure-sealingly and releasably surrounds a first end portion 108 of said drinking conduit 102, whereas a second end portion 110 of the drinking conduit 102 is connected to the lid 94. At its circumferential edge 15 the membrane 92 is provided with an axially extending flexible collar portion 112 that may be compressed and be resilient in an axial direction, axial compression causing the collar portion 112 to flex radially outwards. The collar portion 112 also creates a distance between the membrane 92 and the partition B which define the valve device suction chamber 114. A specific underpressure P2 within the suction chamber 114 causes said compression, after which the flexible collar portion 112 will straighten axially. In order to be resilient axially, the circumference of the collar portion 112 may be provided with axially extending and elastically flexible struts 116, cf. FIGS. 5a-5b. Such struts 116 are arranged to exert a specific resistance to axial compression of the membrane 92, the struts 116 being flexible in a radial direction. After compression the elastic struts 116 will straighten the collar portion 112 axially.

As mentioned, the FIGS. 5a-12b also show different types of sealing elements and different types of stems fixedly arranged to the outflow hole 52 of the membrane 92. With the exception of FIGS. 6a-6b, all figures show only one stem placed in the outflow hole 52.

In FIGS. 5a-5b, FIGS. 9a-9b, FIG. 10 and FIGS. 12a-12b the outflow hole 52 is provided with a stem 11B having a cross-shaped cross section and being secured to the membrane wall around the hole 52, the shape of the stem 118 allowing unobstructed fluid flow through the outflow hole 52.

Figure 5A:
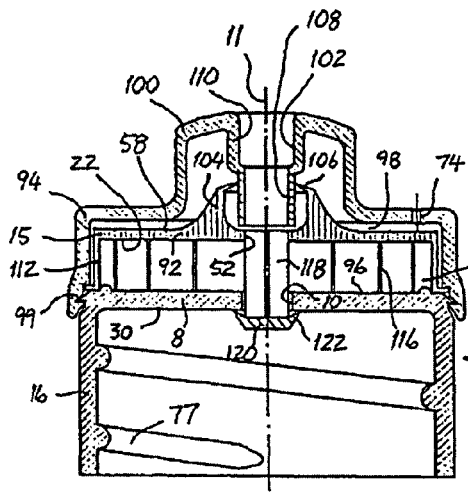
Figure 5B:
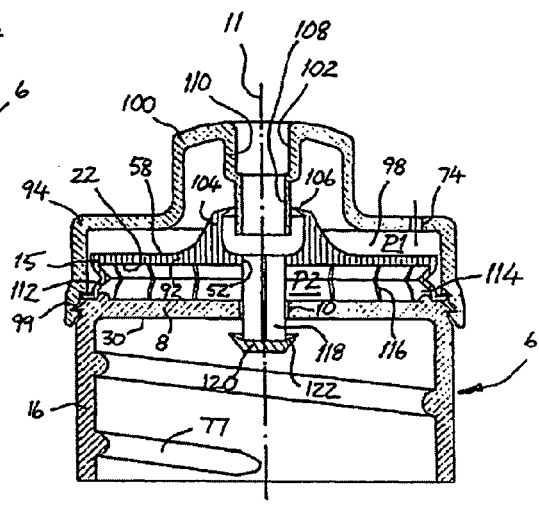
Figure 10:
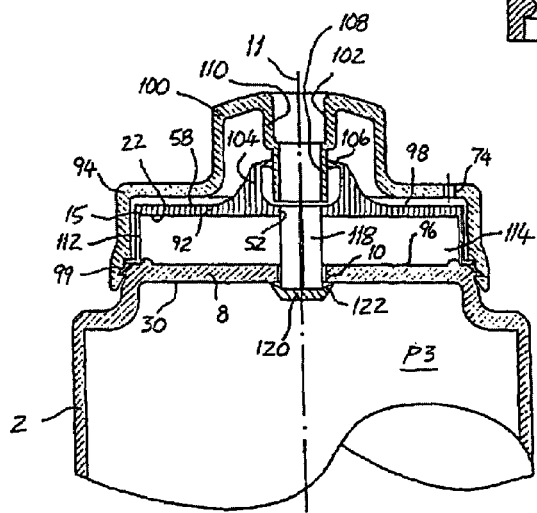

In FIGS. 5a-5b and FIG. 10 the free end of the stem 118 is provided with a flat valve head 120 with a surrounding flexible and peripherally tapered gasket 122. FIG. 5a and FIG. 10 show the valve in its closed position, whereas FIG. 5b shows the valve in its open position, wherein the collar portion 112 is compressed and the struts 116 are flexed radially towards the longitudinal axis 11.

Figure 9A:
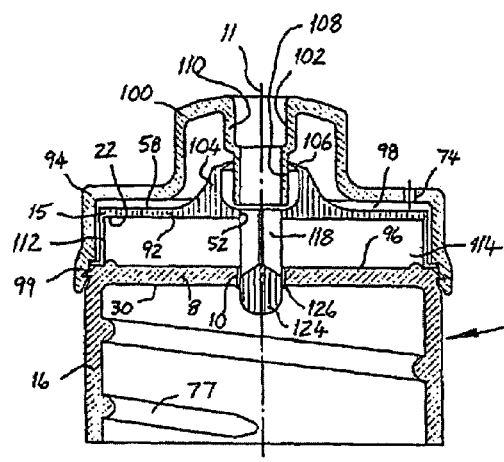
Figure 9B:
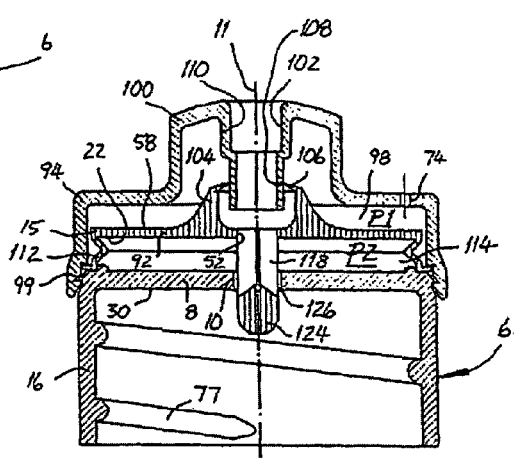

In FIGS. 9a-9b the free end of the stem 11B is provided with a plug-shaped valve head 124 that, when the valve is closed, bears sealingly against a ring gasket 126 formed around the opening 10 of the partition 8, cf. FIG. 9a. When the valve is open, the stem 118 and the valve head 124 have been pushed into the drinking container 2, cf. FIG. 9b.

Figure 12A:
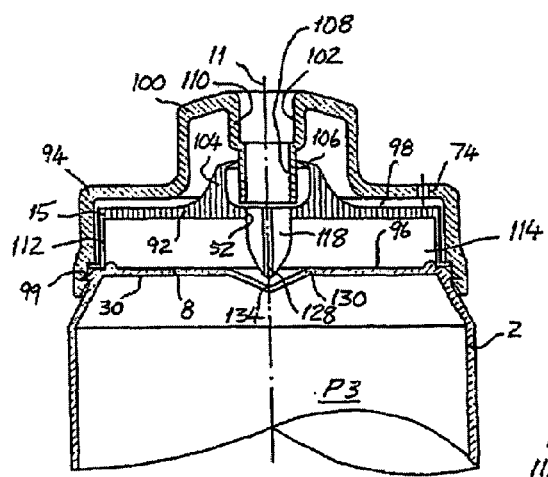
Figure 12B:
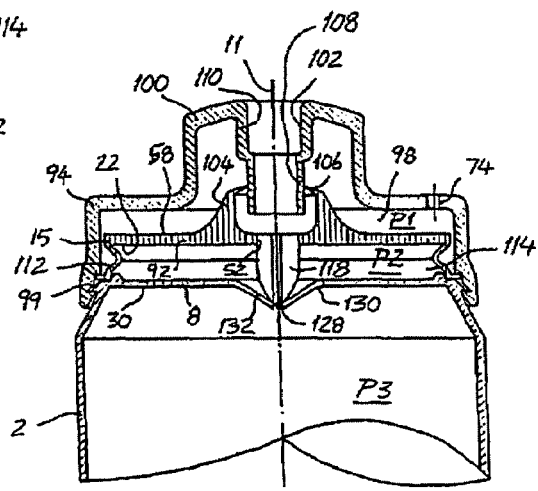

In FIGS. 12a-12b the free end of the stem 118 is provided with a tip 128. At the same time the partition 8 is formed with an elastic yield zone 130 opposite the tip 128. The yield zone 130 consists of completely or partially through-going slots 132 formed into a cross 134 in the partition 8, the cross 134 projecting into the drinking container 2. The valve opens when the membrane 92 imparts a slot-opening force F1 onto the stem tip 128, forcing the slots 132 out and apart, cf. FIG. 12b. When the force F1 ceases, the slots 132 close elastically against each other, cf. FIG. 12a.

Figure 7A:
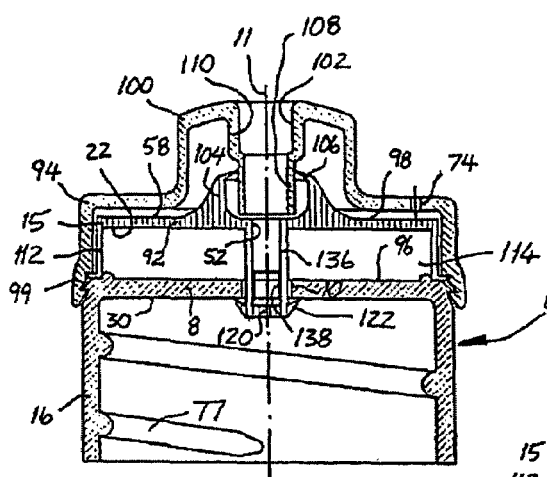
Figure 7B:
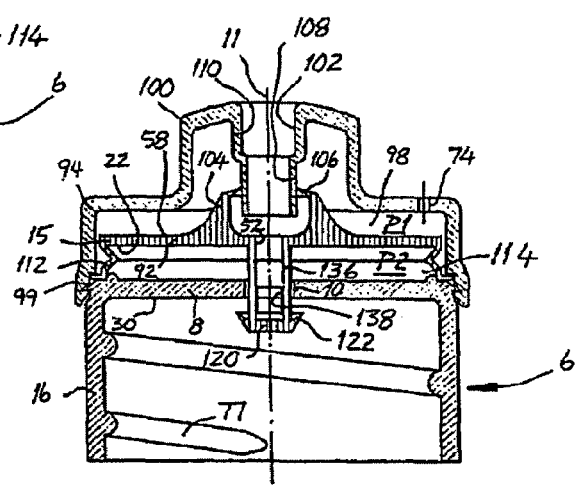

In FIGS. 7a-7b the outflow hole 52 is provided with a tubular stem 136 that, in the tube wall thereof, is provided with at least one opening 138 allowing flow between the drinking container 2 and the drinking conduit 102, and flow towards the suction chamber 114. At its free end the stem 136 is provided with said flat valve head 120 and its ring gasket 122. FIG. 7a and FIG. 7b show the valve in closed position and open position, respectively.

Figure 8A:
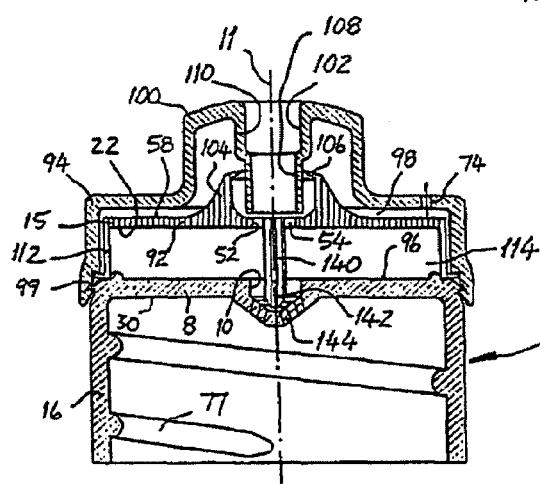
Figure 8B:
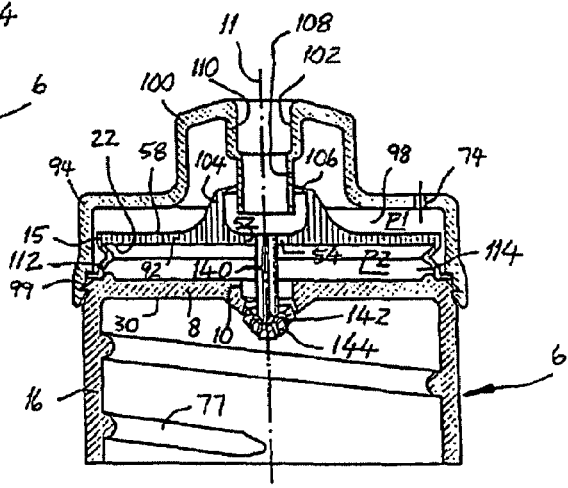

In FIGS. 8a-8b the outflow hole 52 is also provided with a stem 140 of a cross-shaped cross section, which is secured to the membrane wall by means of radial bars 54. The free end of the stem 140 is provided with a tip 142 that extends into the opening 10 of the partition 8 and towards spiral windings 144 covering the opening 10, the spiral windings 144 forming the sealing element of the valve. The windings 144 are prestressed and bear pressure-sealingly against each other when in inactive position, cf. FIG. 8a. When introducing said underpressure P2 into the suction chamber 114 to activate the membrane 92, the stem tip 142 will press axially against the centre of the spiral windings 144. Thereby, the windings 144 are pushed apart and into the drinking container 2, so that the valve opens to fluid outflow, cf. FIG. 8b. Preferably the spiral windings 144 are formed as part of the partition 8.

Figure 11A:
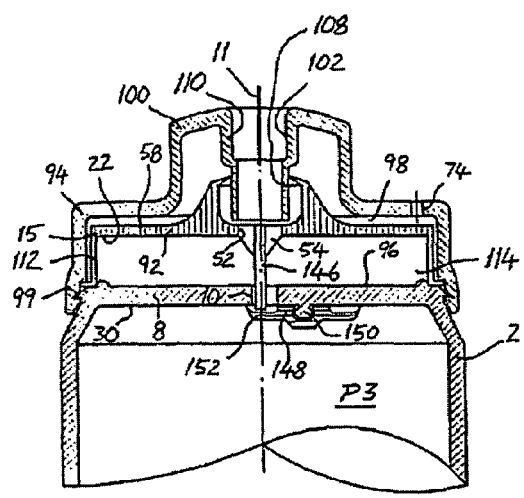
Figure 11B:
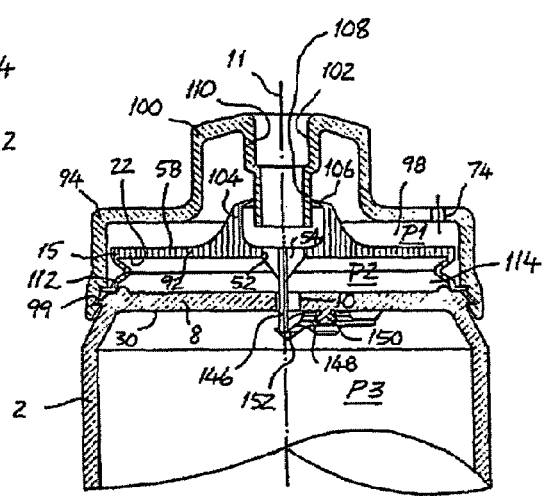

FIGS. 11a-11b also show a stem 146 being secured to the membrane wall by means of radial bars 54. A middle portion of a separate and eccentrically positioned flap seal 148 is releasably connected to a mounting nipple 150 on the inside 30 of the partition 8. In its closed position a first outer segment 152 of the seal 148 covers the opening 10 of the partition 8, cf. FIG. 11a. The valve opens when the stem 146 forces this seal segment 152 into the drinking container 2, cf. FIG. 11b.

Figure 6A:
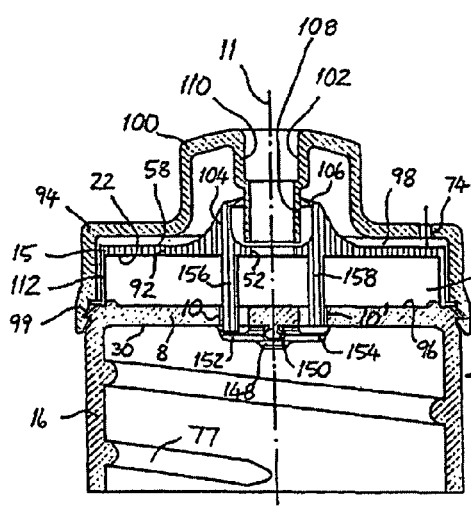
Figure 6B:
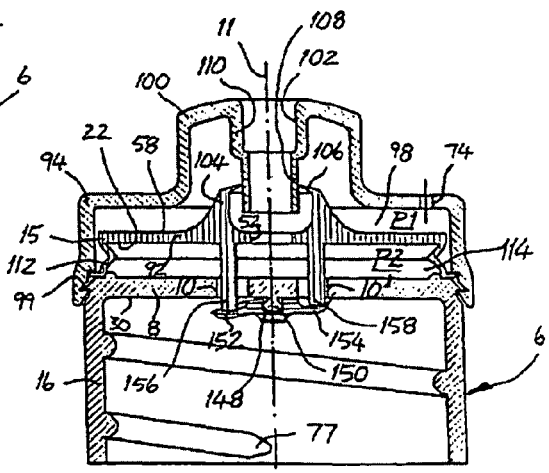

FIGS. 6a-6b show the middle portion of the same flap seal 148 releasably connected to a mounting nipple 150 on the inside 30 of the partition 8. However, the mounting nipple 150 is centred about the axis 11. Moreover, the partition 8 is provided with two wall openings 10, 10', both of which are covered by the flap seal 148. The opening 10 is covered by said first outer seal segment 152, whereas an opposite second outer seal segment 152 covers the opening 10'. A first stem 156 and a second stem 158 are connected to the inside 22 of the membrane 92 and around is outflow hole 52. The stems 156, 158 extend with dissimilar lengths into the wall openings 10 and 10', respectively. Upon valve-opening activation of the membrane 92, the first and longer stem 156 initially will engage and displace the first seal segment 152, whereby fluid outflow through the opening 10 is initiated. Upon further valve-opening axial movement of the membrane 92, the second and shorter stem 15B will also engage and displace the second seal segment 154. By so doing, the valve is opened sequentially and progressively, which may prove particularly useful when the pressure P3 within the drinking container 2 is great.

The FIGS. 13a-18c show exemplary embodiments wherein, in contrast, the valve device membrane is shaped as a drinking spout around a central drinking conduit. In the FIGS. 5a-12b it is the lid 94 that is provided with these components. Moreover, in FIGS. 13a-15e said partition 8 coincides with an end wall of a cap 6, whereas in FIGS. 16a-18c the partition B forms a part of a drinking container 2.

In the FIGS. 13a-18c the membrane is formed with a centred, axially extending and tubular membrane stub that forms an is outward drinking conduit and defines the drinking opening of the membrane, and one end portion thereof being fixedly connected to the upper part of the membrane. Moreover, the membrane is shaped as a drinking spout that surrounds the membrane stub, the membrane being pressure-sealingly connected at its circumference to the partition 8. The membrane thereby defines a suction chamber into which the membrane stub extends. In all of these figures the free end portion of the membrane stub is connected to said cross-shaped stem 118 in a manner allowing through-flow. The stem 118 is passed through said opening 10 of the partition 8, the free end of the stem 11B being provided with said valve head 120 and its peripheral ring gasket 122.

In the FIGS. 13a-14 a membrane 160 is formed with an external, cylindrical drinking spout 162 that surrounds a centred, axially extending membrane stub 164 to which said cross-shaped stem 118 is connected in a manner allowing through-flow. The membrane 160 is also provided with an axially extending flexible collar portion 166 that is connected to the drinking spout 162 via a radially extending membrane portion 167, and which is pressure-sealingly connected to a cap 6 by means of said snap connection 99. The membrane 160 thereby defines a suction chamber 168. The collar portion 166 is arranged to allow axial compression and resiliency, the collar portion 166 flexing radially towards said longitudinal axis 11 upon axial compression. Thereby, the valve opens to fluid outflow. To prevent inadvertent activation of the valve device, the collar portion 166 is provided with axially extending and elastically flexible struts 170 along its circumference, cf. FIG. 13a. When an underpressure P2 is supplied to the suction chamber 168, the struts 170 are arranged to exert a specific resistance to axial compression but little resistance to radial inward flexing. Each strut 170 consists of two axial strut elements 170a, 170b, their adjacent end surfaces 170a' and 170b', respectively, being of complementary form and hinged together at their radially outer sides, cf. FIG. 13a'. Thereby, the strut elements 170a, 170b are arranged to interlock when the valve device is inactive and the collar portion 166 is extended axially. Upon activation and compression of the collar portion 166, the elements 170a, 170b collapse radially via said hinging, cf. FIG. 13b. An enlarged section of this is shown in FIG. 13b. In FIG. 14 a concentric protective housing 172 that is connected to the cap 6, and which is formed from a bracing material, surrounds the collar portion 166. The protective housing 172 may also be arranged as a separate protective ring (not shown in the figures) that is releasably placed around the collar portion 166 of the membrane 160.

The FIGS. 15a-16c also show exemplary embodiments wherein the valve device membrane is shaped as a drinking spout about a central drinking conduit. However, the membrane is not provided with an axially extending flexible collar portion 166.

In FIGS. 15a-15e said partition 8 coincides with an end wall of a cap 6, the membrane being attached directly to the partition 8, for example by means of gluing or heat treatment. In FIGS. 16a-16c the partition 8 forms part of a drinking container 2, the membrane being pressure-sealingly connected to the partition 8 of the drinking container 2 by means of a snap connection 99.

The membrane is formed with a centred, axially extending tubular membrane stub that forms an outward drinking conduit defining the drinking opening of the membrane, and one end portion thereof being fixedly connected to the upper part of the membrane. Thereby, the membrane defines a suction chamber into which the membrane stub projects. In the FIGS. 15a-15c the free end portion of the membrane stub also is connected to said cross-shaped stem 118 in a manner allowing through-flow, the stem 118 being passed through said opening 10 of the partition 8 and being provided with said valve head 120 and ring gasket 122 arranged to close the opening 10.

Figure 15A:
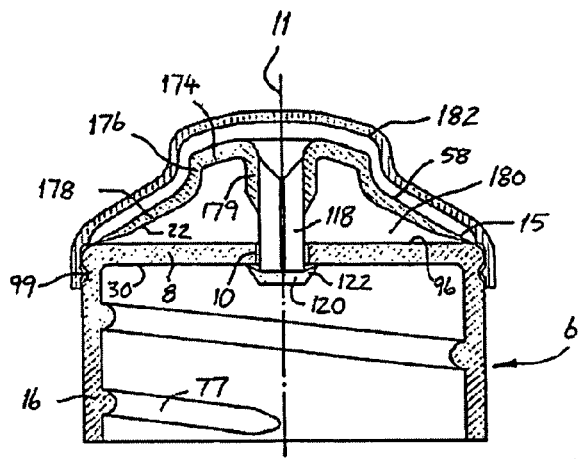
Figure 15B:
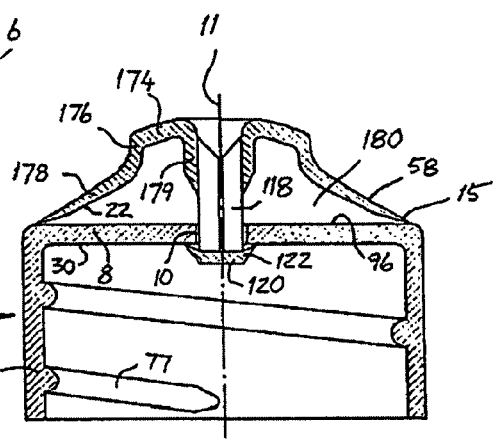
Figure 15C:
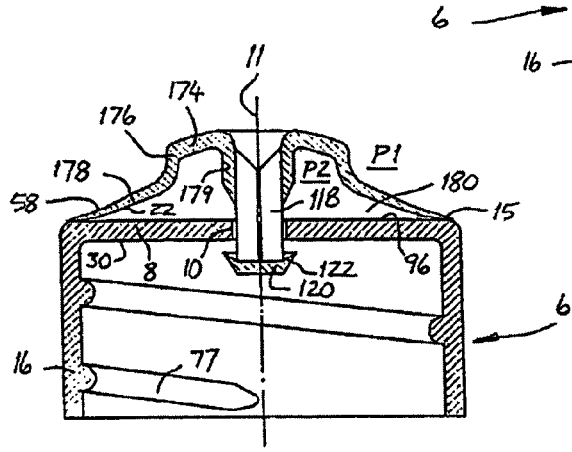
Figure 16A:
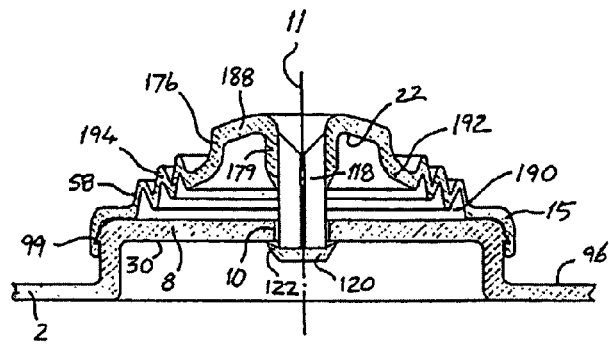
Figure 16B:
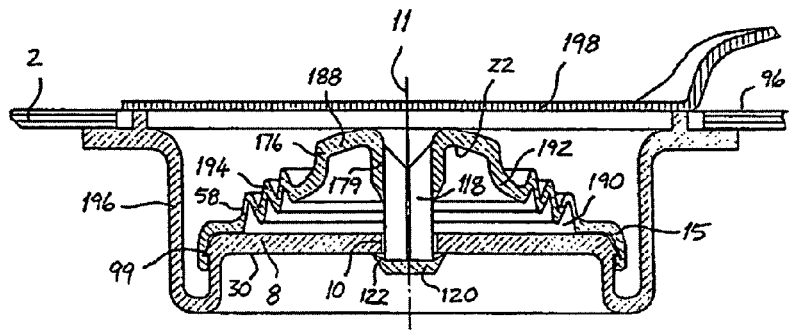
Figure 16C:
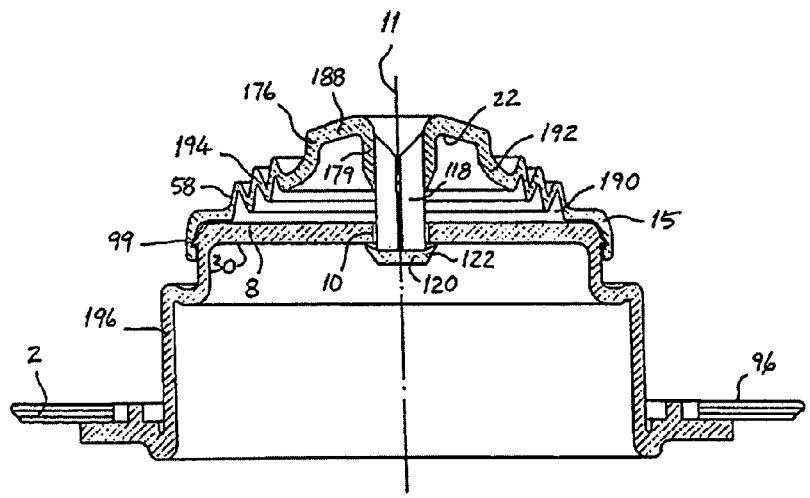

FIG. 15a-15c show a membrane 174 formed with a central projecting drinking spout 176 that, via a sloping flexible membrane portion 178, is placed pressure-sealingly against the partition 8 of the cap 6. The drinking spout 176 surrounds a centred, axially extending membrane stub 179 onto which said cross-shaped stem 118 and valve head 120 are connected in a manner allowing through-flow. The membrane 174 thereby defines a suction chamber 180. Upon pressure activation of the membrane 174, the flexible membrane portion 178 is arranged for resilient movement in the axial direction. When the valve head 120 of the stem 118 is placed supportingly against the partition 8, this membrane flexibility may also be used to prestress the membrane 174 in a pressure-sealing manner against the partition 8. Moreover, FIG. 15c shows the valve in its open position.

In FIG. 15a the membrane 174 is shown covered and surrounded by a protective cover 182, whereby inadvertent activation and contamination of the membrane 174 is prevented. By means of a snap connection 99 the membrane 174 is pressure-sealingly connected to the cap 6.

Figure 15D:
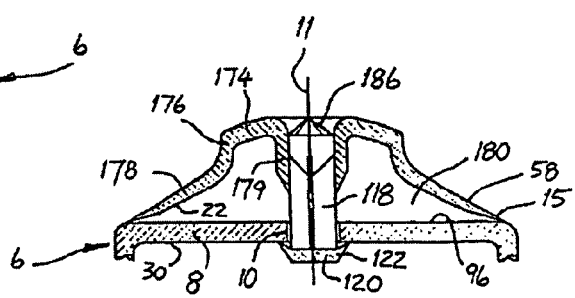
Figure 15E:
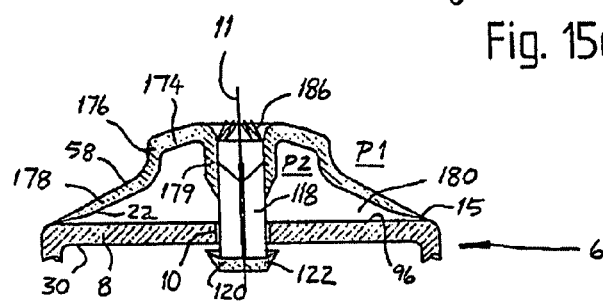

FIGS. 15d-15e show the membrane stub 179 provided with elastic radial flaps 186 along its internal circumference. The free ends of the flaps 186 are arranged to rest closingly against each other when the valve device is inactive. On the other hand, when an underpressure P2 is supplied to the suction chamber 180, the flaps 186 are arranged to flex outward and open in the direction of fluid outflow. The flaps 186 prevent fluid from running out when the valve device is inactive. The flaps 186 may also form a one-way choke device ensuring that the underpressure P2 prevails in the suction chamber 180 for a while after the user has stopped sucking fluid out of the drinking container 2. Thereby, the valve may be kept open for a while thereafter, so that air is gradually admitted into the drinking container 2. Thereby, the valve device is also emptied of fluid remaining therein. The flaps 186 also prevent undesired objects, for example insects, from entering the valve device and the drinking container 2. Moreover, FIG. 15e shows the valve in its open position. FIGS. 16a-16c show a membrane 188 which is also formed with a central projecting drinking spout 176 surrounding a centred, axially extending membrane stub 179 onto which said cross-shaped stem 118 and valve head 120 are connected in a manner permitting through-flow. By means of a snap connection 99 the membrane 188 is pressure-sealingly connected to the partition 8 of the drinking container 2. The membrane 188 thereby defines a suction chamber 190. This membrane 188 too is provided with a sloping membrane portion 192. However, the membrane portion 192 is provided with several concentric annular corrugations 194 arranged be resilient upon movement of the membrane 188.

In FIGS. 16b-16c the valve device is associated with a partition in the form of a fold-in wall portion 196 of a drinking container 2. In FIG. 16b the device is shown folded into the drinking container 2, the folded in wall portion 196 being covered by a protective seal 198. FIG. 16c shows the wall portion 196 in an unfolded state after having removed the seal 198.

FIGS. 17a-18c show a membrane 200 that is provided with several concentric, annular corrugations 202 at the circumferential edge 15 of the membrane 200. The membrane corrugations 202 are arranged in the axial direction, and the membrane 200 is thereby arranged to spring like a bellows in the axial direction. The membrane 200 resembles the membrane 188 according to FIGS. 16a-16c by being provided with a centred, axially extending membrane stub 179 onto which said cross-shaped stem 118 and the valve head 120 are connected in a manner allowing through-flow. The membrane 200 is also provided with a central projecting drinking spout 204 surrounding the membrane stub 179. However, due to said axially extending corrugations 202, the drinking spout 204 is shaped somewhat different than the drinking spout 176 according to FIG. 16a-16c. By means of a snap connection 99 the membrane 200 is pressure-sealingly connected to the outside 96 of a partition 8 in the form of said fold-in wall portion 196 of a drinking container 2, cf. FIGS. 16b-16c. The membrane 200 thereby defines a suction chamber 206.

Figure 17A:
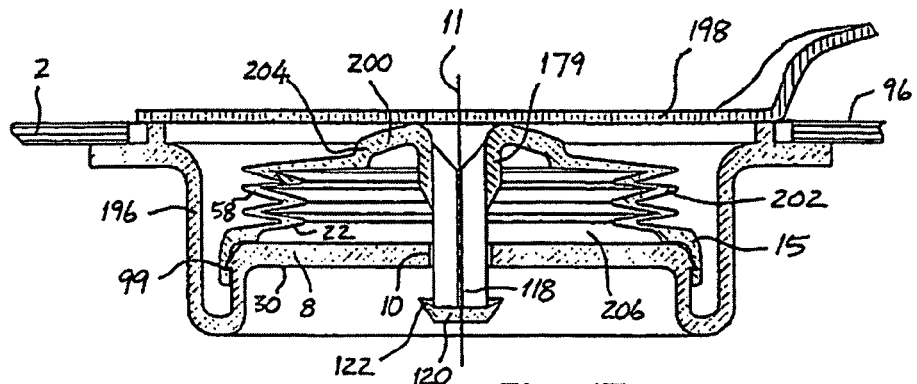
Figure 17B:
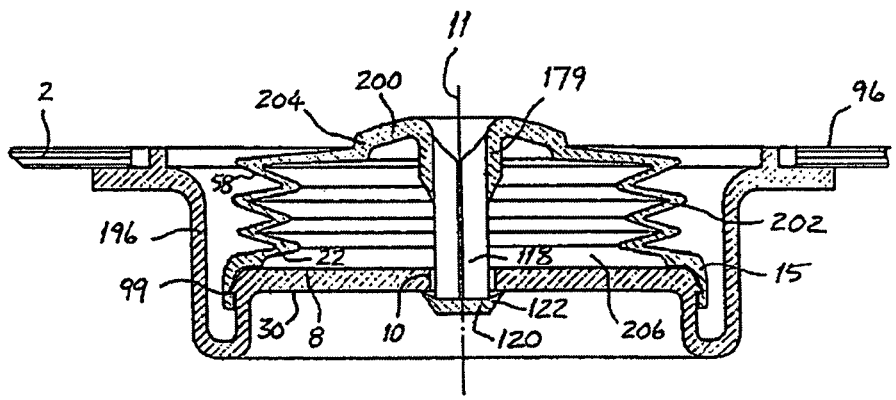

In FIG. 17a the valve device is shown folded into a drinking container, in which the folded in wall portion 196 is covered by said protective seal 198, and in which the membrane corrugations 202 are compressed by the seal 198. Due to this compression the valve is placed in the open position. On the other hand, FIG. 17b shows the valve in its closed position after having removed the seal 198 and having straightened the membrane corrugations 202 in the axial direction. In contrast, FIG. 17c shows a partition in the form of a fold-in wall portion 208 mounted on the outside 96 of the drinking container 2.

Figure 17C:
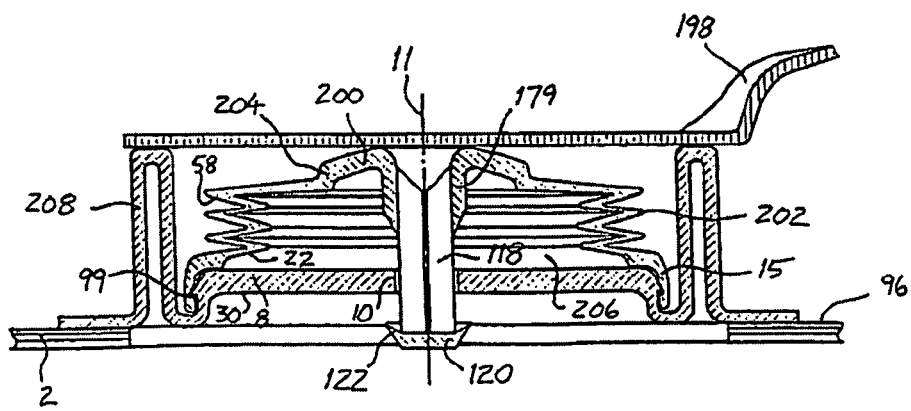
Figure 18A:
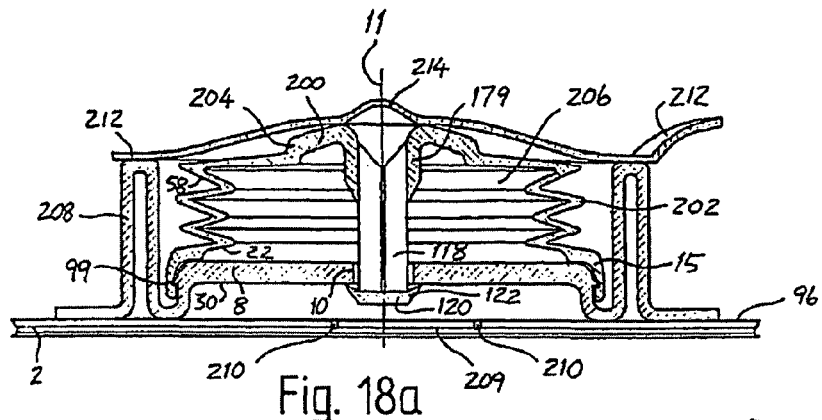
Figure 18B:
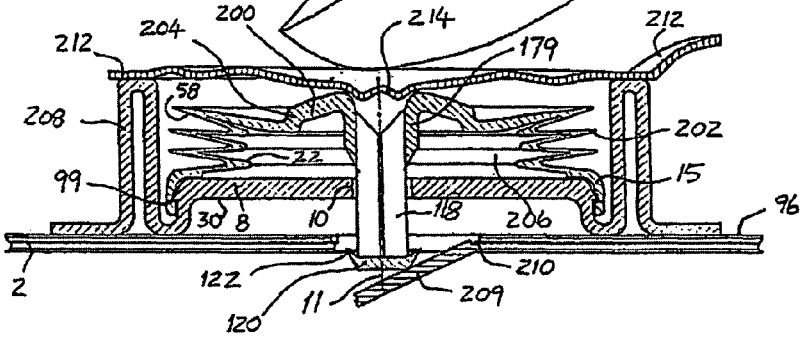
Figure 18C:
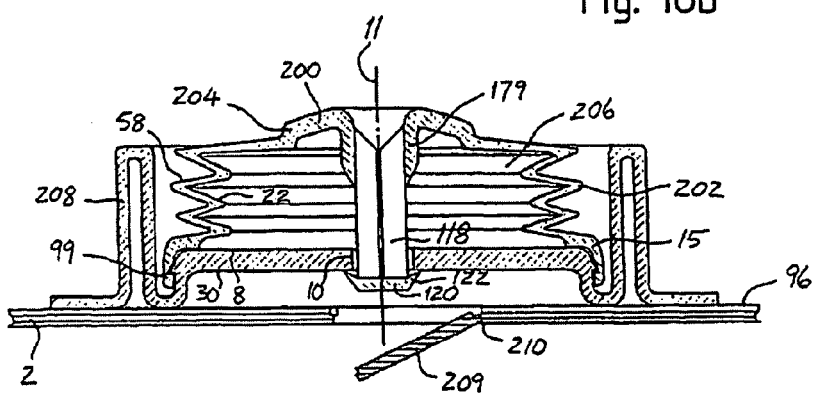

In FIGS. 18a-18c the valve device according to FIGS. 17a-17c and the fold-in wall portion 208 according to FIG. 17c are arranged on the outside 96 of the drinking container 2, the container 2 being, for example, a carton filled with pasteurized liquid. Moreover, a wall area 209 of the drinking container 2 located about the device axis 11 and opposite the device valve head 120 is provided with partial, annular perforations 210, cf. FIG. 18a. A protective seal 212 that is provided with a pressure-activated indicator device 214 opposite the drinking spout 204 covers the valve device and the fold-in wall portion 208. To open the drinking container 2, a user may press a finger 216 against the seal 212 and its indicator device 214. Thereby, the membrane stem 118 is pushed against said wall area 209 of the drinking container 2, so that the wall area 209 is broken loose along the perforations 210 and is pushed into the drinking container 2, cf. FIG. 18b. Simultaneously, the indicator device is deformed 214, so that an indicator pattern appears that indicates opening of the drinking container 2. Then the seal 212 is removed, whereby the valve device is placed in an inactive position ready for use, cf. FIG. 18c.

Figure 19A:
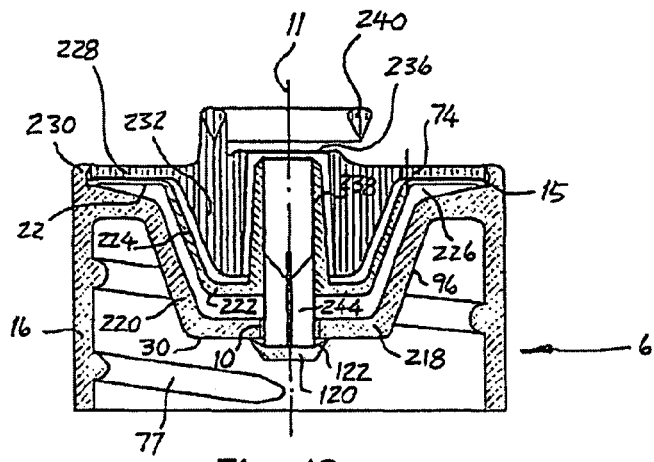
Figure 19B:
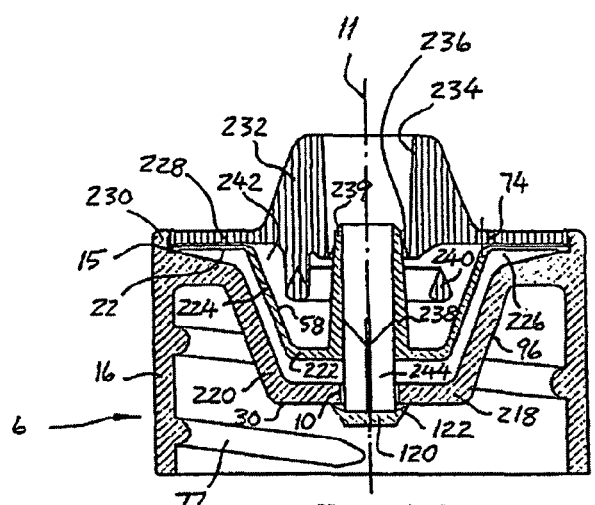
Figure 19C:
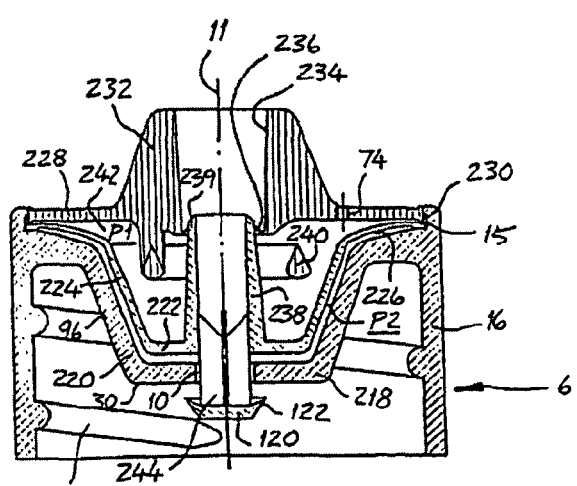

FIGS. 19a-19c show a cap 6 provided with a concentric partition 218. The partition 218 is arranged with a recessed middle portion 220 provided with a central and axial wall opening 10. A membrane 222 is also formed with a recessed middle portion 224 fitting into the recessed middle portion 220 of the partition 218. The membrane 222 is placed at a distance from the partition 218, so that a suction chamber exists 226 between them. Together with an external and invertible lid 228, the membrane 222 is placed pressure-sealingly and releasably within an external housing 230 of the cap 6. The lid 228 is also provided with a vent 74. Moreover, a middle portion of the lid 228 is formed with an axially projecting drinking spout 232 fitting into the recessed middle portion 224 of the membrane 222. The spout 232 is provided with a drinking opening 234 extending axially through it, one end thereof being provided with a breakable seal 236. The membrane 222 is formed with an axially extending tubular membrane stub 23B that projects axially out from the outflow hole 52 of the membrane 222 and away from its suction chamber 226, and that thus extends into the drinking opening 234 of the spout 232. This constitutes the transport or storage position of the lid 228, cf. FIG. 19a, in which position the seal 236 is unbroken and covers the outlet 239 of the membrane stub 238. The lid 228 is also provided with a grip ring 240 projecting, in this position, from the lid 228. Thereby, the lid 228 may be pulled out of the housing 230, whereupon the lid 228 is turned over and put back into its position of use in the housing 230. In the position of use the drinking opening 234 of the drinking spout 232 is placed in a position covering and surrounding an outer portion of the membrane stub 238. Thereby, the seal 236 is broken and exists as a pressure-sealing sliding seal surrounding the membrane stub 232, cf. FIG. 19b, the activation device thereby being prepared for function. In this position an outer chamber 242 between the membrane 222 and the lid 228 also exists, the chamber 242 being pressure-balanced against the ambient pressure P1 via the vent 74 of the lid 228. The membrane stub 232 is also connected to a cross-shaped stem 244 arranged to allow through-flow, and that is passed through the opening 10 of the partition 218. At its free end the stem 244 is provided with said valve head 120 and ring gasket 122. FIG. 19*c* shows the valve device placed in its open position.

FIGS. 20*a*-26*c* show further embodiments of the present valve device, in which the membrane is shaped as a bellows extending concentrically and axially about said longitudinal axis 11. Thereby, the bellows is arranged with a first end portion which is pressure-sealingly associated with the outside of a partition between the valve device and a fluid inside a drinking container 2, the membrane being bracingly associated with a sealing element that opens or closes to fluid outflow. A second and axially opposite end portion of the membrane is shaped as a drinking opening. Between the first and second end portions the bellows defines a drinking conduit, and the internal cavity of the bellows constitute a suction chamber. The bellows is arranged with flexible zones that capable of contracting peripherally and radially. By means of bracing elements the bellows contraction is converted into a valve-opening force F1.

FIGS. 20*a*-20*c*, FIGS. 22*a*-22*c*, FIG. 23 and FIG. 25 all show a membrane bellows 246 extending concentrically and axially. Along its circumference the bellows 246 is provided with axially extending corrugations 248 that have an axially bracing effect on the bellows 246. Moreover, the membrane bellows 246 is reinforced with force-transmitting axial struts 250. By means of the corrugations 248 the bellows 246 may be contracted peripherally and radially. To allow radial contraction, the circumference of the bellows 246 is formed with an outer articulated zone 252, a intermediate articulated zone 254 and an inner articulated zone 256. The struts 250 are linked together via the intermediate articulated zone 254. The inner articulated zone 256 is placed at a first end portion 258 of the bellows 246.

Furthermore, in these exemplary embodiments the articulated zone 256 forms a circumferential edge 15 of the membrane bellows 246 that is associated with an opening 10 of the partition 8. However, the outer articulated zone 252 is placed at an axially opposite second end portion 260 of the bellows 246, forming a drinking opening 262 therein. The internal cavity of the bellows 246 forms a suction chamber 264. When supplying an underpressure P2 to the suction chamber 264, the bellows 246 contracts and extends in the axial direction, whereby an axial valve-opening force F1 is exerted.

Figure 20A:
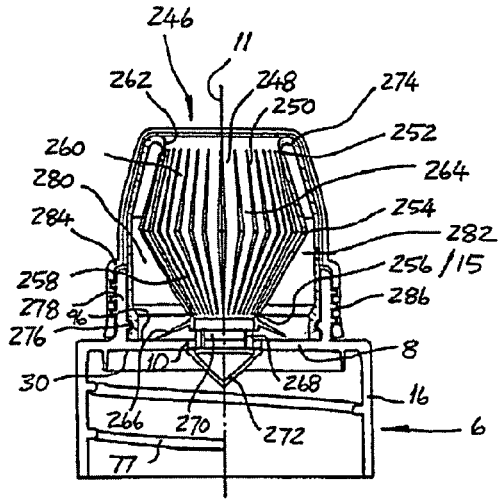
Figure 20B:
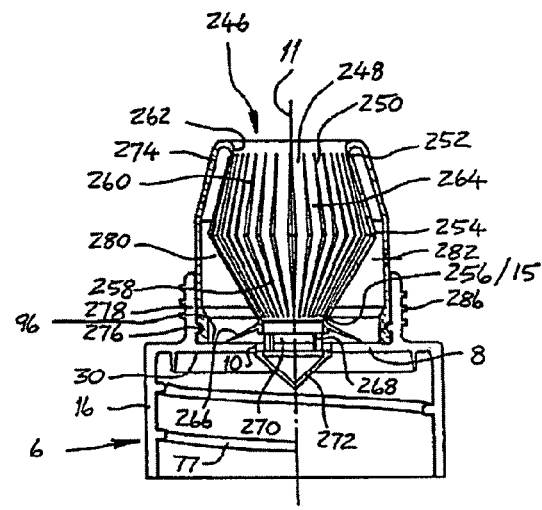
Figure 20C:
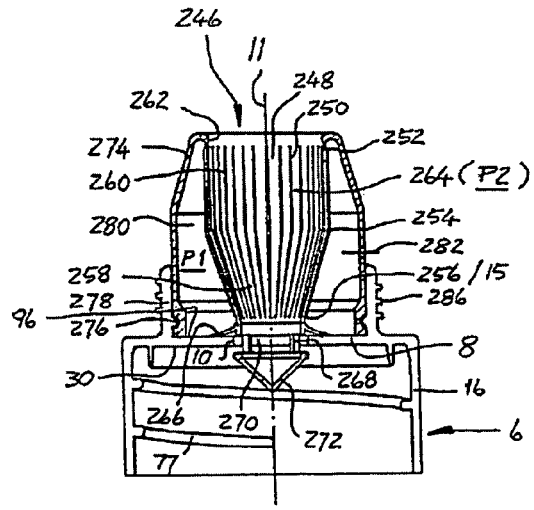

In FIGS. 20*a*-20*c* the first end portion 258 of the membrane bellows 246 is provided with a peripheral and flexible sealing edge 266 that connects said membrane circumference edge 15 to an opening 10 in a partition 8 of a cap 6, the sealing edge 266 being positioned on the outside 96 of the partition 8 and pressure-sealingly surrounding the opening 10. The end portion 258 is also connected to a hollow stem 268 with stem openings 270 in a manner permitting through-flow. At its free end the stem 268 is provided with a conical valve head 272 arranged to enable closing of the wall opening 10, cf. FIG. 20*b*. Other types of stems and valve heads may also be used in connection with the membrane bellows 246. However, the second end portion 260 is fixed relative to the partition 8, so that the bellows is extended axially towards the wall opening 10 upon contraction, thereby pushing the valve head 272 into its open position, cf. FIG. 20*c*. The end portion 260 is fixed to the partition 8 by means of a concentric and rigid jacket 274 surrounding the bellows 246. One end of the jacket 274 is connected to the end portion 260, whereas its other end is pressure-sealingly connected to a connecting portion 276 of an external cap housing 278. The bellows 246 and jacket 274 define an outer chamber 280 that communicates with the ambient pressure P1 through a vent 282 in the jacket 274. In FIG. 20*a* the jacket 274 and bellows 246 are surrounded by a protective cover 284 that is connected to a further connecting portion 286 externally on the cap housing 27B.

Figure 21:
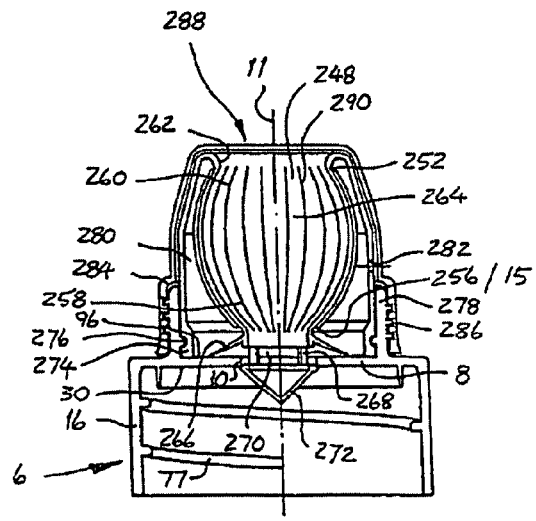

FIG. 21 shows a membrane bellows 288 resembling the previously mentioned bellows 246. By means of axial elastic struts 290 the membrane bellows 288 is provided with a curvilinear form in its axial direction, whereby an intermediate articulated zone of the bellows 288 is redundant. The bellows 288 is also placed in an external cap housing 278 surrounded by a jacket 274.

Figure 22A:
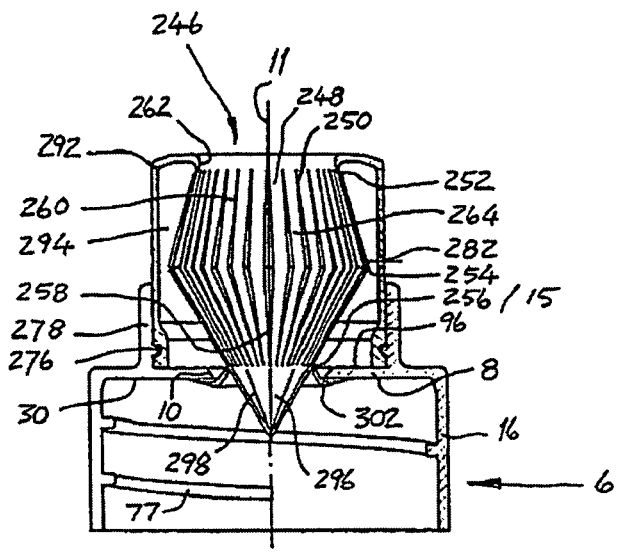
Figure 22B:
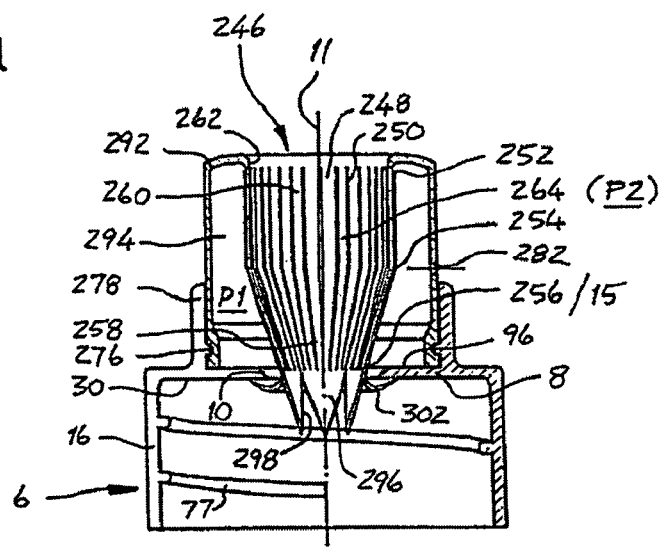
Figure 22C:
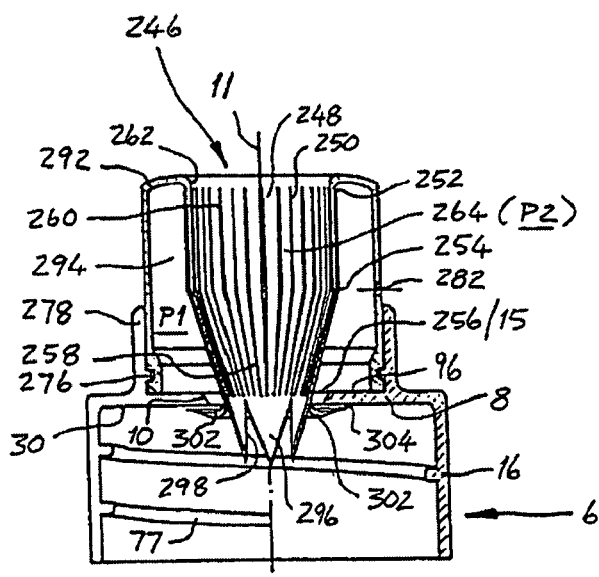

In FIGS. 22*a*-22*c* the bellows 246 is also surrounded by a concentric and rigid jacket 292 of a somewhat different shape than the jacket 274 according to FIG. 20, as this jacket 292 is also pressure-sealingly connected to the connecting portion 276 of the cap housing 278. The jacket 292 is provided with a vent 282 and defines an outer chamber 294. In these figures the first end portion 258 of the membrane bellows 246 terminates in a beak in the form of a converging cone tip 296, cf. FIG. 22*a*. The tip 296 is provided with axially extending closable slot openings 298 that emerge from said inner articulated zone 256 at the first end portion 258 of the bellows 246. When influenced by said underpressure P2 and axial force F1, the cone tip 292 is exposed to a beak-opening torque, the slot openings 298 thereby being forced out and apart, cf. FIG. 22*b*. The cone tip 296 and its slot openings 298 thereby form the sealing element of the valve. The first end portion 258 is provided with a peripheral and flexible sealing edge 302 that is arranged pressure-sealingly and releasably around said wall opening 10. However, in this exemplary embodiment the sealing edge 302 bears against the inside 30 of the partition 8 of the cap 6. Thereby, an air inlet 304 is formed between the wall opening 10 and said beak when the bellows 246 is compressed and the beak is open, cf. FIG. 22*c*. When closing the beak, the sealing edge 302 will re-seal against the partition 10, whereby the air inlet 304 is closed.

FIG. 23 shows the bellows 246 and the cone tip 296 according to FIG. 22. In this exemplary embodiment the first end portion 258 is provided with a broader peripheral and flexible sealing edge 306. The second end portion 260 is connected to a concentric and rigid jacket 308 provided with a radial flange 310 at its free end. The flange 310 thereby forms a partition between the bellows 246 and a drinking container 2. The flange 310 is connected around a larger opening 312 of the drinking container 2, the sealing edge 306 being placed releasably and pressure-sealingly against the inside 30 of the flange 310. This jacket 308 is also provided with a vent 282 and defines an outer chamber 314.

Figure 25:
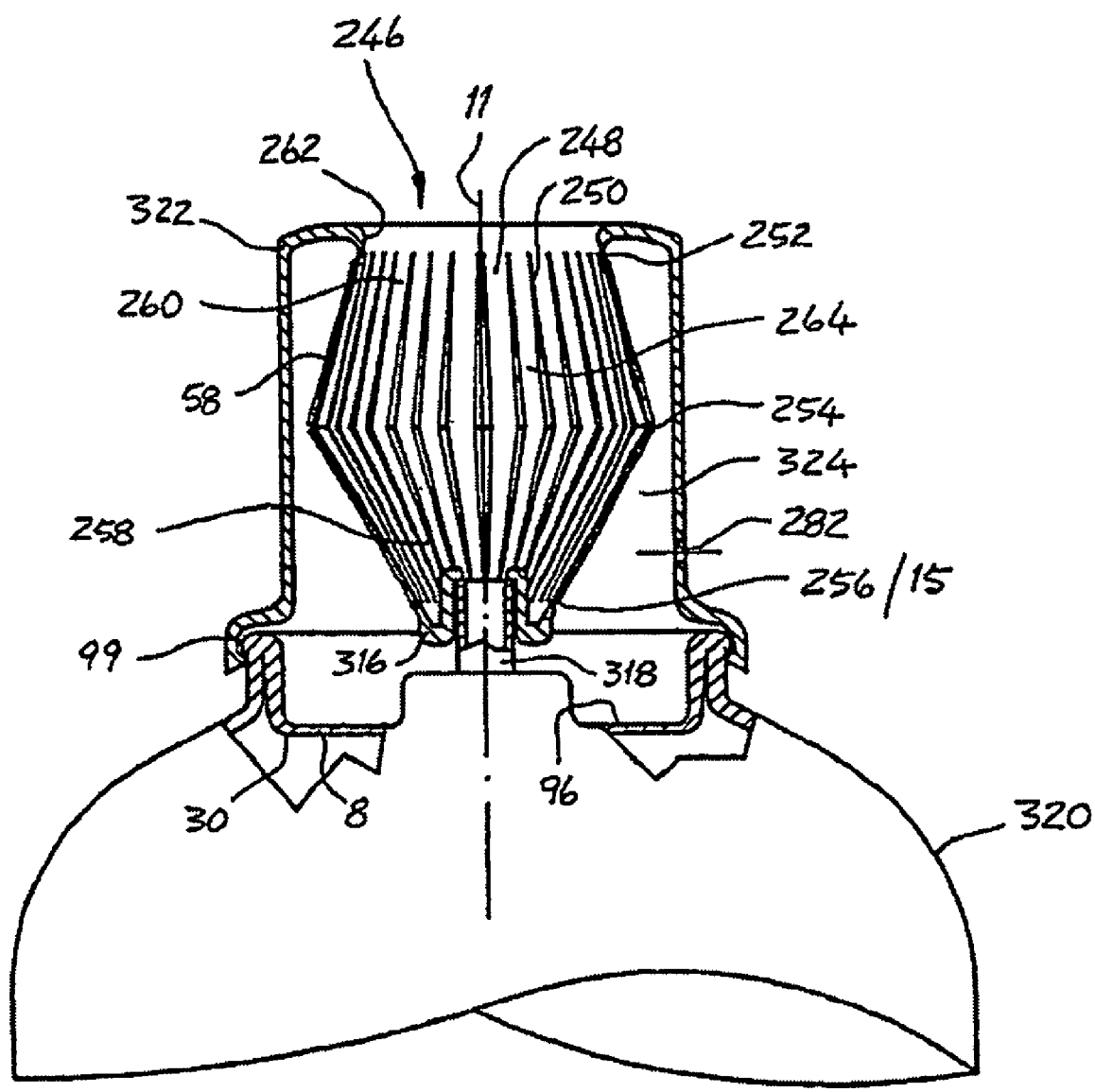

FIG. 25 shows an alternative embodiment of the membrane bellows 246, in which its first end portion 258 is provided with a connecting sleeve 316 which fits around an outlet stub 316 of a valve of an aerosol bottle 310. Upon activation of the bellows 246, the stub 318 is pushed axially into the bottle 320, opening the valve to the outflow of fluid. A surrounding jacket 322 with a vent 282 defines an outer chamber 324 between the bellows 246 and the jacket 322, the jacket 322 being pressure-sealingly connected at its free end to the aerosol bottle 320 via a snap connection 99.

FIGS. 24*a*-24*b* show the jacket 308, the flange 310 and the opening 312 of the drinking container 2 according to FIG. 23. However, in this exemplary embodiment a non-corrugated flexible membrane bellows 326 is used. At its first end portion 258 the bellows 326 also terminates in a cone tip 328 that is provided with axially extending and closable slot openings 330. The slot openings 330 form a cross 332, cf. FIGS. 24*a'*-24*b'* which both show radial sections through the valve device. Between the slot openings 330 the inside of the cone tip 328 is provided with radial, triangular struts 334 that converge in the cone tip 328. At axially opposite triangle corners, the struts 334 are attached within a concentric, intermediate articulated zone 336 of the membrane bellows 326. Opposite the intermediate triangle corners of the struts 334, the outside of the bellows 326 is provided with a peripheral and flexible sealing edge 338 placed releasably and pressure-sealingly against the flange 310. Between the articulated zone 336 and the second end portion 260, the bellows 326 is formed with a smooth membrane wall 340 that, in its inactive position, is parallel with the longitudinal axis 11, cf. FIG. 24a. The bellows 326 surrounds an internal suction chamber 342, whereas the jacket 308 defines an outer chamber 344 communicating via its vent 282 with the ambient pressure P1. When an underpressure P2 is supplied to the chamber 342, the bellows 326 contracts radially, cf. FIG. 24b. Thereby, a beak-opening torque is supplied to the cone tip 328, forcing the slot openings 330 out and apart, cf. FIG. 24b', whereby the valve opens.

Figure 26A:
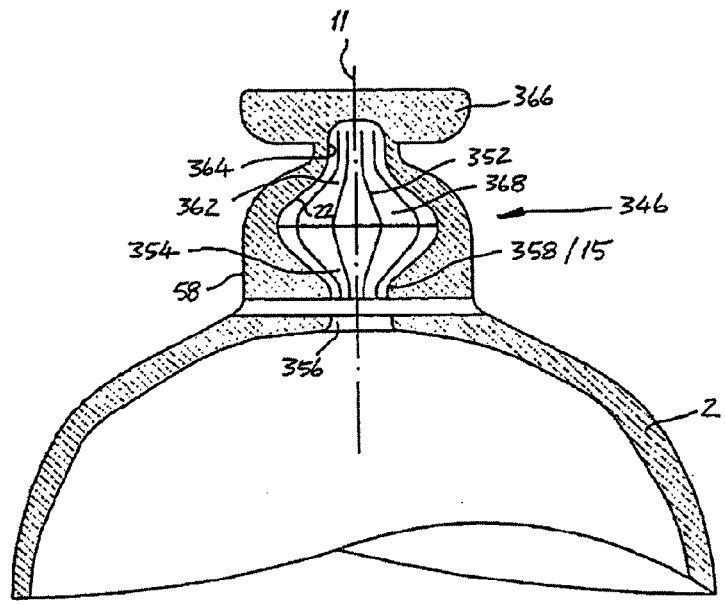
Figure 26B:
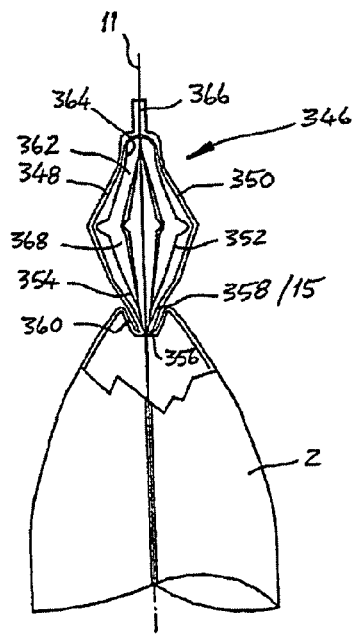
Figure 26C:
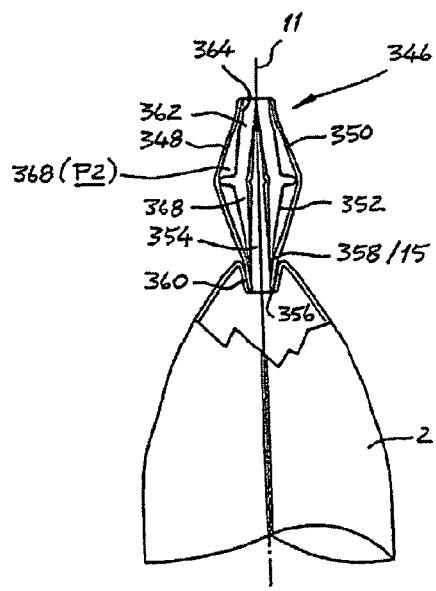

FIG. 26a-26c show a membrane bellows 346 formed by two plastic foils or plastic-coated foils 348, 350 welded together and provided with axially extending reinforcements 352. These reinforcements 352 may consist of axial bracing elements or bracing corrugations in the foils 348, 350. A first end portion 354 of the bellows 346 is formed with a beak that converges into an expandable membrane ring 356. The ring 356 emerges from an inner articulated zone 358 at the first end portion 354 of the bellows 346, the ring 356 forming the sealing element of the valve. In this exemplary embodiment the articulated zone 358 forms a circumferential edge 15 of the membrane bellows 346 that merges into the expandable membrane ring 356. The membrane ring 356 is also provided with a circumferential collar 360 that is connected to the drinking container 2, and which thus forms said partition between the bellows 346 and the container 2. A second and axially opposite end portion 362 of the bellows 346 is shaped as a drinking opening 364. Initially, a seal 366 closes the drinking opening 364, cf. FIGS. 26a-26b which show two different views of the drinking container 2. To provide access to the valve device and the fluid inside the drinking container 2, the seal 366 is pulled off before use. Thereby, the drinking opening 364 is exposed, so that access is provided to a suction chamber 368 defined by the bellows 346. Upon supplying an underpressure P2 to the suction chamber 368, the bellows 346 is contracted radially, whereby a beak-opening torque forces the membrane ring 356 radially outwards and opens it, cf. FIG. 26c.

FIGS. 27a-27e show a further exemplary embodiment, in which the present valve device is placed in a concentric and closed cap 370 provided with a radial inlet tube 372 and a diametrically placed radial outlet tube 374. The inlet tube 372 may be connected to a drinking straw 376, whereas the outlet tube 374 may be shaped as a drinking spout 378, cf. FIG. 27e. Alternatively, the inlet tube 372 may be provided with threads 379, cf. FIG. 27d. The threads 379 may be screwed into a soft drinking container, for example a carton or drinking bag (not shown). Thereby, the cap 370 may be releasably connected to a drinking container 2.

Figure 27A:
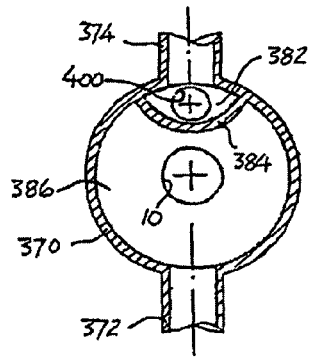
Figure 27B:
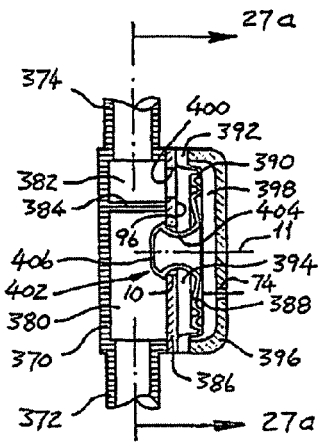

The inlet tube 372 and the outlet tube 374 are connected to an inlet chamber 380 and an outlet chamber 382, respectively, both of which are placed in the closed cap 370. The two chambers 380, 382 are positioned next to each other, separated by an axially directed cap wall 384. The cap wall 384 is shown clearly in section in FIG. 27a, cf. FIG. 27b showing a section line 27a-27a through the chambers 380, 382. Moreover, the cap 370 is provided with a radial partition 386 separating the chambers 380, 382 from a flat membrane 388 disposed on the outside 96 of the partition 386. The membrane 388 is provided with annular corrugations 390 at its circumferential edge 392. Furthermore, the membrane 388 is pressure-sealingly connected to the partition 386 and positioned at a distance therefrom, whereby a suction chamber 394 exists between the two. An outer lid 396 also pressure-sealingly surrounds the membrane 388. The lid 396 is placed at a distance from the membrane 388, thereby defining an outer chamber 398 communicating with the ambient pressure P1 via a vent 74 in the lid 396. The partition 386 is provided with a central wall opening 10 connecting said inlet chamber 380 to the suction chamber 394. Moreover, the partition 386 is provided with an eccentrically positioned drinking opening 400 extending outwards and connecting the suction chamber 394 with said outlet chamber 382, cf. FIG. 27b-27e.

Figure 27C:
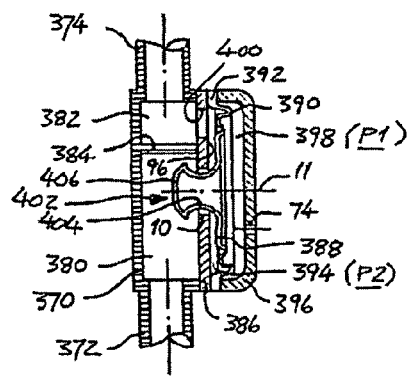
Figure 27D:
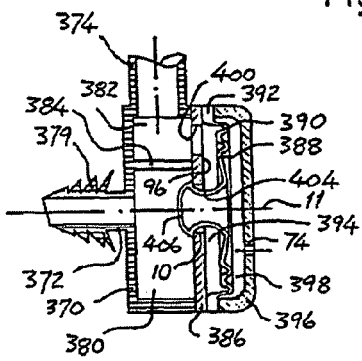
Figure 27E:
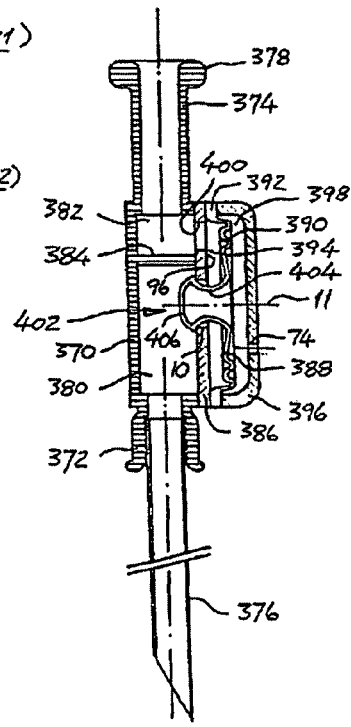

A central portion of the membrane 388 is formed with a braced axial membrane extension 402 extending through the central opening 10 of the partition 386. Opposite the opening 10, the membrane extension 402 is formed with a restricted middle portion 404, and at its free end portion the membrane extension 402 is formed with a widened collar portion 406 which may fit pressure-sealingly against the inside 30 of the partition 386. Thereby, the membrane extension 402 works as both a valve stem and a valve head. In FIG. 27c the membrane 388 is shown activated when an underpressure P2 is supplied to the suction chamber 394. Thereby, the membrane extension 402 is pushed axially into the inlet chamber 380, opening to the outflow of fluid via, among other things, said eccentric drinking opening 400. Arrows in FIG. 27c indicate the direction of outflow.

The invention claimed is:

1. A valve device structured for releasable connection to a drinking container containing a fluid, the valve device comprising:
    a valve that is movable between an open position and a closed position for controlling fluid discharge from the drinking container when connected thereto, wherein the valve comprises a pressure-responsive, movable element; at least one bracing element; and a sealing element, the bracing element connecting the movable element to the sealing element such that movement of the movable element causes movement of the sealing element; and
    a cap enclosing the valve and comprising a partition wall having an inside and an outside, and wherein the partition wall is provided with a sealing element opening and a drinking opening;
    wherein the sealing element opening in the partition wall is structured for releasable connection to the drinking container;
    wherein the movable element is disposed on the outside of the partition wall and between the partition wall and the enclosing cap, whereby a suction chamber is defined between the movable element and the partition wall;
    wherein the movable element has at least one surface exposed to pressure in the suction chamber, and at least one opposite surface exposed to ambient pressure outside the cap;
    wherein the bracing element extends through the sealing element opening so as to locate the sealing element on the inside of the partition wall;
    wherein the sealing element, when in the closed position, seals against the inside of the partition wall, and wherein the sealing element, when in the open position, does not seal against the inside of the partition wall; and
    wherein application of a predetermined amount of suction at the drinking opening reduces the pressure in the suction chamber below ambient pressure so as to produce a differential pressure across the movable element, whereby the differential pressure acts on the movable element to move the movable element in the direction of the suction chamber and thereby force the sealing element and thus the valve out of the closed position.

2. The valve device according to claim 1, wherein the sealing element opening in the partition wall, on the inside thereof, is connected to an inlet tube structured for releasable connection to the drinking container; and wherein the drinking opening in the partition wall, on the inside thereof, is connected to an outlet tube.

3. The valve device according to claim 2, wherein the inlet tube is connected to the sealing element opening via an inlet chamber arranged within the cap;

wherein the outlet tube is connected to the drinking opening via an outlet chamber arranged within the cap; and wherein the inlet chamber and the outlet chamber are separated from each other by means of a cap wall extending from the partition wall of the cap.

4. The valve device according to claim 1, comprising a membrane that forms the movable element, bracing element and sealing element.

5. The valve device according to claim 4, wherein the movable element comprises at least one flexible zone that is resilient upon movement of the movable element.

6. The valve device according to claim 5, wherein the flexible zone comprises at least one concentric annular membrane corrugation that is positioned between an axis that is transverse to the partition wall and a peripheral edge of the movable element.

7. The valve device according to claim 4, wherein the surface of the movable element that is exposed to the suction chamber has a substantially planar shape; and wherein the planar shape is substantially parallel to the partition wall.

8. The valve device according to claim 4, wherein the bracing element comprises a braced axial extension of the membrane extending through the sealing element opening in the partition wall;

wherein the braced axial extension is formed with a restricted middle portion positioned opposite the sealing element opening in the partition wall; and wherein the sealing element comprises a widened collar portion of the membrane capable of bearing pressure-sealingly against the inside of the partition wall.

9. The valve device according to claim 2, comprising a membrane that forms the movable element, bracing element and sealing element.

10. The valve device according to claim 9, wherein the movable element comprises at least one flexible zone that is resilient upon movement of the movable element.

11. The valve device according to claim 10, wherein the flexible zone comprises at least one concentric annular membrane corrugation that is positioned between an axis that is transverse to the partition wall and a peripheral edge of the movable element.

12. The valve device according to claim 9, wherein the surface of the movable element that is exposed to the suction chamber has a substantially planar shape; and wherein the planar shape is substantially parallel to the partition wall.

13. The valve device according to claim 9, wherein the bracing element comprises a braced axial extension of the membrane extending through the sealing element opening in the partition wall;

wherein the braced axial extension is formed with a restricted middle portion positioned opposite the sealing element opening in the partition wall; and wherein the sealing element comprises a widened collar portion of the membrane capable of bearing pressure-sealingly against the inside of the partition wall.

14. The valve device according to claim 3, comprising a membrane that forms the movable element, bracing element and sealing element.

15. The valve device according to claim 14, wherein the movable element comprises at least one flexible zone that is resilient upon movement of the movable element.

16. The valve device according to claim 15, wherein the flexible zone comprises at least one concentric annular membrane corrugation that is positioned between an axis that is transverse to the partition wall and a peripheral edge of the movable element.

17. The valve device according to claim 14, wherein the surface of the movable element that is exposed to the suction chamber has a substantially planar shape; and wherein the planar shape is substantially parallel to the partition wall.

18. The valve device according to claim 14, wherein the bracing element comprises a braced axial extension of the membrane extending through the sealing element opening in the partition wall;

wherein the braced axial extension is formed with a restricted middle portion positioned opposite the sealing element opening in the partition wall; and wherein the sealing element comprises a widened collar portion of the membrane capable of bearing pressure-sealingly against the inside of the partition wall.

\* \* \* \* \*